United States Patent [19]
Duyao et al.

[11] Patent Number: 5,538,844
[45] Date of Patent: Jul. 23, 1996

[54] TRANSPORT PROTEIN GENE FROM THE HUNTINGTON'S DISEASE REGION

[75] Inventors: Mabel P. Duyao, Cambridge; Marcy E. MacDonald, Lexington; James F. Gusella, Framingham, all of Mass.

[73] Assignee: The General Hospital Corporation, Boston, Mass.

[21] Appl. No.: 35,928

[22] Filed: Mar. 23, 1993

[51] Int. Cl.$^6$ .................. C12Q 1/68; C12P 21/06; C07H 19/00; C07H 21/00
[52] U.S. Cl. .................. 435/6; 435/69.1; 435/240.2; 435/320.1; 530/350; 536/22.1; 536/23.1; 536/23.4; 536/23.5
[58] Field of Search .................. 435/6, 19.1, 240.2, 435/320.1; 530/350; 536/22.1, 23.1, 23.4, 23.5

[56] References Cited

PUBLICATIONS

Daly, C. B., "Genetic cause is identified for Huntington's disease", *The Washington Post*, Mar. 24, 1993.
Goldberg, Y. P. et al., "Identification of an Alu retrotransposition event in close proximity to a strong candidate gene for Huntington's disease", *Nature* 362:270–373 (Mar. 25, 1993).
Goodfellow, P. N., "Planting alfalfa and cloning the Huntington's disease gene", *Cell* 72:817–818 (Mar. 26, 1993).
Little, P., "The end of the beginning", *Nature* 362:408–409 (Apr. 1, 1993).
MacDonald, M. E. et al., "A novel gene containing a trinucleotide repeat that is expanded and unstable on Huntington's disease chromosomes", *Cell* 72:971–983 (Mar. 26, 1993).
Morell, V., "Huntington's gene finally found", *Science* 260:28–30 (Apr. 2, 1993).
Richards, R. I. et al., "Evidence of founder chromosomes in fragile X syndrome", *Nature Genetics* 1:257–260 (Jul. 1992).
Altschul, S. F. et al., "Basic local alignment search tool", *J. Mol. Biol.* 215:403–410 (1990).
Ambrose, C. et al., "A novel G protein–coupled receptor kinase cloned from 4p16.3", *Hum. Mol. Genet.* 1(9):697–703 (1992).
Bates, G. P. et al., "Define physical limits of the Huntington disease gene candidate region", *Am. J. Hum. Genet.* 49:7–16 (1991).
Bates, G. P. et al., "Characterization of a yeast artificial chromosome contig spanning the Huntington's disease gene candidate region", *Nature Genet.* 1:180–187 (Jun. 1992).
Buckler, A. J. et al., "Exon amplification: a strategy to isolate mammalian genes based on RNA splicing", *Proc. Natl. Acad. Sci. USA* 88:4005–4009 (May 1991).
Gusella, J. F., "Chapter 3—Huntington's disease", *Adv. Hum. Genet.* 20:125–151 (1991).

Levy, S. B. "Tetracycline resistance determinants are widespread", *Am. Soc. Microbiol. News* 54(8):418–421 (1988).
Lin, C. S. et al., "New DNA markers in the Huntington's disease gene candidate region", *Somat. Cell Mol. Genet.* 17(5):481–488 (1991).
Liu, Y. et al., "A cDNA that suppresses MPP$^+$ toxicity encodes a vesicular amine transporter", *Cell* 70:539–551 (Aug. 21, 1992).
MacDonald, M. E. et al., "The Huntington's disease candidate region exhibits many different haplotypes", *Nature Genet.* 1:99–103 (May 1992).
MacDonald, M. E. et al., "A somatic cell hybrid panel for localizing DNA segments near the Huntington's disease gene", *Genomics* 1:29–34 (1987).
MacDonald, M. E. et al., "Recombination events suggest potential sites for the Huntington's disease gene", *Neuron* 3:183–190 (Aug. 1989).
Marger, M. D. and Saier, M. H. Jr., "A major superfamily of transmembrane facilitators that catalyse uniport, symport and antiport", *TIBS* 18:13–20 (Jan. 1993).
Martin, J. B. and Gusella, J. F., "Huntington's disease: pathogenesis and management", *N. Engl. J. Med.* 315(20):1267–1276 (Nov. 13, 1986).
McClatchey, A. I. et al., "The genomic structure of the human skeletal muscle sodium channel gene", *Hum. Mol. Genet.* 1(7):521–527 (1992).
Smith, B. et al., "Isolation of DNA markers in the direction of the Huntington disease gene from the G8 locus", *Am. J. Hum. Genet.* 42:335–344 (1988).
Snell, R. G. et al., "A recombination event that redefines the Huntington disease region", *Am. J. Hum. Genet.* 51:357–362 (1992).
Taylor, S. A. M. et al., "Cloning of the α–adducin gene from the Huntington's disease candidate region of chromosome 4 by exon amplification", *Nature Genet.* 2:223–227 (Nov. 1992).
Yamaguchi, A. et al., "Stoichiometry of metal–tetracycline/ H$^+$ antiport mediated by transpson Tn10–encoded tetracycline resistance protein in *Escherichia coli*", *FEBS Lett.* 282(2):415–418 (May 1991).

*Primary Examiner*—Robert A. Wax
*Assistant Examiner*—Hyosuk Kim
*Attorney, Agent, or Firm*—Sterne, Kessler, Goldstein & Fox

[57] ABSTRACT

The present invention relates, in general, to a novel transport protein, IT10C3. In particular, the present invention relates to nucleic acid molecules coding for IT10C3; IT10C3 polypeptides; recombinant nucleic acid molecules; cells containing the recombinant nucleic acid molecules; antisense IT10C3 nucleic acid constructs; antibodies having binding affinity to an IT10C3 polypeptide; hybridomas containing the antibodies; nucleic acid probes for the detection of IT10C3 nucleic acid; a method of detecting IT10C3 nucleic acid or polypeptide in a sample; and kits containing nucleic acid probes or antibodies.

10 Claims, 8 Drawing Sheets

| | |
|---|---:|
| CGCCCCTTTA GGGTGCTCGC CGGCTGTCGG GTGTGGGGGT ATGCCAGGCC CCGGAGGACT | 60 |
| CGGCTTCCCC GCTAACCCGA CCCGCCGCAC CCCACCCAGG CCAGGTCAGA GCAGCCCACC | 120 |

```
ATG GGA TGG GGA GGG GGT GGA GGC TGC ACC CCC CGC CCA CCC ATC CAC        168
Met Gly Trp Gly Gly Gly Gly Gly Cys Thr Pro Arg Pro Pro Ile His
 1           5                   10                  15

CAG CAG CCG CCG GAG CGC CGC GTG GTC ATC GTT GTC TTT CTC GGC CTC        216
Gln Gln Pro Pro Glu Arg Arg Val Val Ile Val Val Phe Leu Gly Leu
             20                  25                  30

CTG CTG GAC CTC CTG GCC TTC ACG CTG CTG CTG CCC CTG CTG CCC GGG        264
Leu Leu Asp Leu Leu Ala Phe Thr Leu Leu Leu Pro Leu Leu Pro Gly
             35                  40                  45

CTG TTG GAG AGC CAC GGC CGT GCC CAC GAC CCC CTC TAT GGC TCC TGG        312
Leu Leu Glu Ser His Gly Arg Ala His Asp Pro Leu Tyr Gly Ser Trp
 50                  55                  60

CAG GGC GGG GTG GAC TGG TTT GCC ACC GCC ATC GGG ATG CCA GTG GAG        360
Gln Gly Gly Val Asp Trp Phe Ala Thr Ala Ile Gly Met Pro Val Glu
 65                  70                  75                  80

AAG AGG TAC AAC AGT GTC CTG TTC GGA GGT CTC ATT GGC TCG GCA TTC        408
Lys Arg Tyr Asn Ser Val Leu Phe Gly Gly Leu Ile Gly Ser Ala Phe
                 85                  90                  95

TCT GTC CTG CAG TTT CTG TGT GCG CCA CTC ACT GGG GCC ACC TCT GAC        456
Ser Val Leu Gln Phe Leu Cys Ala Pro Leu Thr Gly Ala Thr Ser Asp
                 100                 105                 110

TGC TTG GGG AGG CGC CCG GTG ATG CTG CTG TGC CTG ATG GGT GTG GCC        504
Cys Leu Gly Arg Arg Pro Val Met Leu Leu Cys Leu Met Gly Val Ala
             115                 120                 125

ACC TCA TAT GCA GTC TGG GCC ACC TCT CGG AGC TTT GCG GCC TTC CTG        552
Thr Ser Tyr Ala Val Trp Ala Thr Ser Arg Ser Phe Ala Ala Phe Leu
             130                 135                 140

GCC TCC AGG CTG ATT GGG GGC ATC AGC AAA GGG AAC GTC AGC CTC TCC        600
Ala Ser Arg Leu Ile Gly Gly Ile Ser Lys Gly Asn Val Ser Leu Ser
145                 150                 155                 160
```

FIG.3A

```
ACG GCC ATC GTT GCT GAC CTG GGC TCG CCT CTG GCC CGC AGT CAA GGC    648
Thr Ala Ile Val Ala Asp Leu Gly Ser Pro Leu Ala Arg Ser Gln Gly
            165                 170                 175
ATG GCG GTC ATT GGG GTG GCC TTC TCA CTG GGC TTC ACC CTG GGC CCT    696
Met Ala Val Ile Gly Val Ala Phe Ser Leu Gly Phe Thr Leu Gly Pro
            180                 185                 190
ATG CTC GGA GCC TCC CTG CCC CTG GAA ATG GCA CCC TGG TTT GCC CTG    744
Met Leu Gly Ala Ser Leu Pro Leu Glu Met Ala Pro Trp Phe Ala Leu
            195                 200                 205
CTC TTC GCA GCC TCC GAC CTG CTG TTC ATC TTC TGC TTC CTG CCA GAG    792
Leu Phe Ala Ala Ser Asp Leu Leu Phe Ile Phe Cys Phe Leu Pro Glu
            210                 215                 220
ACG CTG CCC CTG GAG AAA CGG GCG CCC TCT ATC GCC CTG GGG TTC CGT    840
Thr Leu Pro Leu Glu Lys Arg Ala Pro Ser Ile Ala Leu Gly Phe Arg
225                 230                 235                 240
GAT GCG GCT GAT CTG CTC AGC CCC CTG GCC CTG CTG CGC TTC TCG GCT    888
Asp Ala Ala Asp Leu Leu Ser Pro Leu Ala Leu Leu Arg Phe Ser Ala
                245                 250                 255
GTC GCT CGT GGC CAG GAC CCA CCC TCT GGA GAC AGG CTC AGC AGC CTG    936
Val Ala Arg Gly Gln Asp Pro Pro Ser Gly Asp Arg Leu Ser Ser Leu
                260                 265                 270
CGC CGC CTG GGC CTA GTC TAC TTC CTC TAC CTC TTC CTG TTC TCG GGC    984
Arg Arg Leu Gly Leu Val Tyr Phe Leu Tyr Leu Phe Leu Phe Ser Gly
            275                 280                 285
CTG GAG TAC ACG CTG AGC TTC CTC ACA CAC CAG CGC TTC CAG TTC AGT   1032
Leu Glu Tyr Thr Leu Ser Phe Leu Thr His Gln Arg Phe Gln Phe Ser
        290                 295                 300
AGC CTA CAG CAG GGG AAG ATG TTT TTC CTC ATC GGC CTC ACC ATG GCC   1080
Ser Leu Gln Gln Gly Lys Met Phe Phe Leu Ile Gly Leu Thr Met Ala
305                 310                 315                 320
ACC ATC CAG GGT GCC TAT GCC CGG CGG ATC CAC CCT GGC GGG GAA GTT   1128
Thr Ile Gln Gly Ala Tyr Ala Arg Arg Ile His Pro Gly Gly Glu Val
                325                 330                 335
```

FIG.3B

| | |
|---|---|
| GCT GCC GTG AAG CGG GCC CTC CTG CTG CTG GTG CCC GCC TTC CTC CTC<br>Ala Ala Val Lys Arg Ala Leu Leu Leu Leu Val Pro Ala Phe Leu Leu<br>           340                  345                350 | 1176 |
| ATC GGC TGG GGA CGT TCT CTG CCC GTG CTG GGC CTG GGG CTG CTG CTC<br>Ile Gly Trp Gly Arg Ser Leu Pro Val Leu Gly Leu Gly Leu Leu Leu<br>           355                  360                365 | 1224 |
| TAC TCC TTT GCC GCC GCC GTT GTG GTG CCC TGC CTG TCC TCC GTG GTC<br>Tyr Ser Phe Ala Ala Ala Val Val Val Pro Cys Leu Ser Ser Val Val<br>           370                  375                380 | 1272 |
| GCT GGC TAT GGC TCA CCA GGG CAG AAG GGC ACG GTC ATG GGT ACA CTG<br>Ala Gly Tyr Gly Ser Pro Gly Gln Lys Gly Thr Val Met Gly Thr Leu<br>385                  390                395                400 | 1320 |
| CGC AGC CTA GGT GCT CTG GCC AGG GCC GCG GGG CCC CTG GTG GCC GCT<br>Arg Ser Leu Gly Ala Leu Ala Arg Ala Ala Gly Pro Leu Val Ala Ala<br>                 405                  410                415 | 1368 |
| TCA GTG TAC TGG CTG GCC GGG GCC CAG GCC TGC TTC ACC ACG TGG TCC<br>Ser Val Tyr Trp Leu Ala Gly Ala Gln Ala Cys Phe Thr Thr Trp Ser<br>                 420                  425                430 | 1416 |
| GGG CTC TTT TTG CTC CCC TTC TTC CTC CTG CAG AAG CTG AGT TAC CCG<br>Gly Leu Phe Leu Leu Pro Phe Phe Leu Leu Gln Lys Leu Ser Tyr Pro<br>           435                  440                445 | 1464 |
| GCA CAG ACG CTC AAG GCT GAG TAGCTGAGCC ACTGTGCCCA GGCTGTGGGC<br>Ala Gln Thr Leu Lys Ala Glu<br>           450                  455 | 1515 |
| ACCAGGCAGA GTGGGAGCCT AGGTCAGGCC CCTGCCCACT GCCTGACCCC CACCCCCCGC | 1575 |
| CAGTCCAGGG AGACCCTGTG GGTGGGGGCC GGCCCCTAAG CAGGAAGCTC AGGCAGCTCC | 1635 |
| TCCAGACTTA CTTACTCCTT CAGTGACTCC GAGCTGCAGC ACTCCAAGGC TGTCAGGGCT | 1695 |
| TCTGTTTGTT TTTTAAACTA TGCACCAGGT TTCTGATGAT GAAATAAAGC ACCTGTTTGT | 1755 |
| TTTAAAAAAA AAAAAAAAAA AAAAAAAAAA AAA | 1788 |

FIG.3C

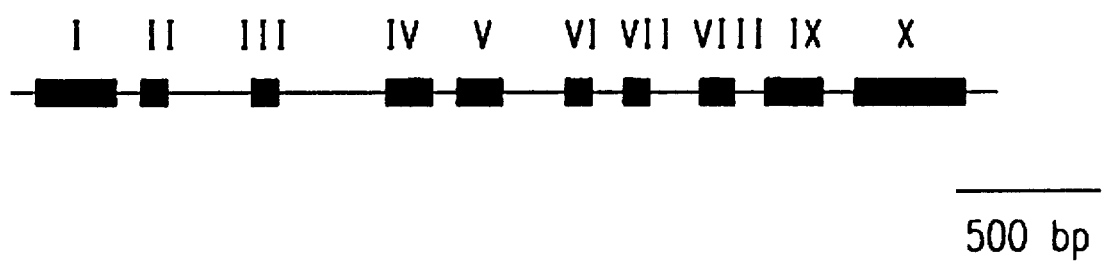

FIG.5A

| EXON | EXON/INTRON | INTRON (bp) | INTRON/EXON | EXON |
|------|-------------|-------------|-------------|------|
| I | GCCCAC/gtgagt | 88 | ccctag/GACCCC | II |
| II | TCGGAG/gtatgg | 287 | tctcag/GTCTCA | III |
| III | TGCCTG/gtatgt | 384 | gggcag/ATGGGT | IV |
| IV | GGCATG/gtaagt | 87 | ccctag/GCGGTC | V |
| V | AAACGG/gtaggg | 197 | ccacag/GCGGTC | VI |
| VI | AGACAG/taagga | 108 | cccagg/GCTCAG | VII |
| VII | CAGTAG/gtgggt | 160 | tcccag/CCTACA | VIII |
| VIII | AAGCGG/gtaggg | 88 | ctgcag/GCCCTC | IX |
| IX | CTTCAG/gtaggg | 108 | ccgcag/TGTACT | X |

```
                            TM1
TCR2    3   SNNALIVILGTVTILDAVGIGLVMPVLPGLLRDIVHSDSIASHY.........     45
            ::|||:  :||  || |:::||||||  |    |:   |
IT10C3  21  ERRVVIVVFLGLLLDLLAFTLLLPLLPGLLES..HGRAHDPLYGSWQGGV         68

TM2
TCR2    46  .........GVLLALYALMQFLCAPVLGALSDRFGRRP                     74
                     ||:|||||   || ||  ||   :||||
IT10C3  69  DWFATAIGMPVEKRYNSVLFGGLIGSAFSVLQFLCAPLTGATSDCLGRRP            118

TM3                              TM4
TCR2    75  VLLASLLGATIDYAIMATTPVLWILYAGRIVAGITGATGAVAGAYIADIT            124
            |:|  | ||  |:|  ||    ||  :|  :|||  :
IT10C3  119 VMLLCLMGVATSYAYWATSRSFAAFLASRLIGGISKGNVSLSTAIVADLG            168

TM6
TCR2    125 DGEDRARHFGLMSACFGVGMVAGPVAGGLLGAISLHAPFLAAAVLNGLNL            174
              ::|                ||:||   ||:   | ::  :
IT10C3  169 SPLARSQGMAVIGVAFSLGFTLGPMLGASL.PLEM.APWFALLFAASDLL            216

TCR2    175 LLGCFLMQESHKGERRPMPLRAFNPVSSFRWARGMTIVAALMTVFFIMQL            224
            ::|||                       ||:    ::  ::
IT10C3  217 FIFCFL.........PETLPLEKRAPSIALGFRDAADLLSPLALLRFSAVA           258
```

5,538,844

TRANSPORT PROTEIN GENE FROM THE HUNTINGTON'S DISEASE REGION

STATEMENT OF GOVERNMENT RIGHTS IN THE INVENTION

Part of the work performed during development of this invention utilized U.S. Government funds. The U.S. Government has certain rights in this invention.

BACKGROUND OF THE INVENTION

1. Field of the Invention

The present invention relates, in general, to a novel transport protein, IT10C3. In particular, the present invention relates to nucleic acid molecules coding for IT10C3; IT10C3 polypeptides; recombinant nucleic acid molecules; cells containing the recombinant nucleic acid molecules; antisense IT10C3 nucleic acid constructs; antibodies having binding affinity to an IT10C3 polypeptide; hybridomas containing the antibodies; nucleic acid probes for the detection of IT10C3 nucleic acid; a method of detecting IT10C3 nucleic acid or polypeptide in a sample; and kits containing nucleic acid probes or antibodies.

2. Background Information

Huntington's disease (HD) is a familial neurodegenerative disorder that afflicts about 1/10,000 individuals (Martin, J. B. and Gusella, J. F., *N. Engl. J. Med.* 315:1267–1276 (1986); Gusella, J. F., *Adv. Hum. Genet.* 20:125–151 (1991)). It is inherited in an autosomal dominant manner and is characterized by choreiform movements, dementia, and cognitive decline. The disorder usually has a mid-life onset, between the ages of 30 to 50 years, but may in some cases begin very early or much later in life. The symptoms are progressive and death ensues 10 to 20 years after onset, most often as the result of secondary complications of the movement disorder. Post-mortem examination of the brains of HD individuals has revealed a selective loss of neurons that most dramatically affects the striatum. The biochemical cause of this neuronal loss which underlies the symptoms of HD has not yet been discovered. Thus, an intensive effort has been mounted to apply location cloning techniques to identify the nature of the genetic defect.

The HD gene has been mapped to a 2.2 Mb region, flanked by the loci D4S126 and D4S98 in the terminal cytogenetic subband of the short arm of human chromosome 4 (MacDonald, M. E. et al., *Neuron* 3:183–190 (1989); Bates, G. P. et al., *Am. J. Hum. Genet.* 49:7–16 (1991); Snell, R. G. et al., *Am. J. Hum. Genet.* 51:357–362 (1992)). Analysis of linkage disequilibrium on HD chromosomes has revealed that the disorder is associated with a wide array of marker haplotypes, but has suggested a 500 kb segment of the candidate region between D4S180 and D4S182 as the most probable location of the genetic defect (MacDonald, M. E. et al., *Nature Genet.* 1:99–103 (1992)). The task of isolating all the transcripts from the candidate region remains a daunting one, despite the availability of cloned genomic DNA (Lin, C. S. et al., *Somat. Cell Mol. Genet.* 17:481–488 (1991); Bates, G. P. et al., *Nature Genetics* 1:180–187 (1992)). However, the recent development of the "exon amplification" technique, which targets the isolation of potential coding regions from cloned genomic DNA, may be used to search for candidate genes (Buckler, A. J. et al., *Proc. Natl. Acad. Sci. USA* 88:4005–4009 (1991)). A novel G protein-coupled receptor kinase and the human α-adducin gene (ADDA) were previously identified by applying this procedure to the region between D4S127 and D4S182 in the HD candidate region (Ambrose, C. et al., *Hum. Mol. Genet.* 1:697–703 (1992); Taylor, S. A. M. et al., *Nature Genet.* 2:223–227 (1992)). The present invention provides a second gene within the same cosmid as the ADDA locus. This novel gene encodes a protein with strong amino acid sequence similarity to a superfamily of transporters typified by tetracycline resistance proteins (Marger, N. D. and Saier, M. H. Jr., *TIBS* 18:13–20 (1993)).

SUMMARY OF THE INVENTION

Recognizing the importance of identifying and characterizing genes within the Huntington's disease region of chromosome 4, the inventors have employed a powerful new method, exon amplification (Buckler et al., *Proc. Natl. Acad. Sci. USA* 88:4005–4009 (1991)) to isolate coding sequences from the region. Exon amplification of cosmid Y24, which maps distal to D4S95 within the Huntington's disease region (cite 11), has led to the isolation of cDNA clone IT10C3.

Sequence analysis revealed IT10C3 to be a novel member of a superfamily of transporters, including the tetracycline efflux proteins. The discovery of this novel transporter protein and the gene encoding same adds to the recognized "Major Facilitator Superfamily" that play a crucial role in controlling protein transport. It also provides the isolation of a novel expression product of a gene within the Huntington's disease region.

Accordingly, the invention provides IT10C3.

The invention also provides an isolated nucleic acid molecule coding for a polypeptide comprising an amino acid sequence corresponding to IT10C3, or at least 7 contiguous amino acids thereof.

The invention further provides a substantially pure polypeptide comprising an amino acid sequence corresponding to IT10C3, or at least 7 contiguous amino acids thereof.

The invention also provides a nucleic acid probe for the detection of the presence of IT10C3 in a sample.

The invention further provides a method of detecting IT10C3 nucleic acid in a sample.

The invention also provides a kit for detecting the presence of IT10C3 nucleic acid in a sample.

The invention further provides a recombinant nucleic acid molecule comprising, 5' to 3', a promoter effective to initiate transcription in a host cell and the above-described isolated nucleic acid molecule.

The invention also provides a recombinant nucleic acid molecule comprising a vector and the above-described isolated nucleic acid molecule.

The invention further provides a recombinant nucleic acid molecule comprising a transcriptional region functional in a cell, a sequence complimentary to an RNA sequence encoding an amino acid sequence corresponding to the above-described polypeptide, and a transcriptional termination region functional in said cell.

The invention also provides a cell that contains the above-described recombinant nucleic acid molecule.

The invention further provides an organism that contains the above-described recombinant nucleic acid molecule.

The invention also provides an antibody having binding affinity to an IT10C3 polypeptide, or a binding fragment thereof.

The invention further provides a method of detecting an IT10C3 polypeptide in a sample.

The invention also provides a method of measuring the amount of IT10C3 in a sample.

The invention further provides a diagnostic kit comprising a first container means containing the above-described antibody, and a second container means containing a conjugate comprising a binding partner of said monoclonal antibody and a label.

The invention also provides a hybridoma which produces the above-described monoclonal antibody.

Further objects and advantages of the present invention will be clear from the description that follows.

BRIEF DESCRIPTION OF THE DRAWINGS

FIG. 3. Composite cDNA sequence of IT10C3 (SEQ ID NO:1). The 1788 base composite DNA sequence was derived from the IT10C3 cDNAs shown in FIG. 1. The predicted amino acid sequence of 455 residues (SEQ ID NO:2) is shown below the DNA sequence (SEQ ID NO:1), with the stop codon denoted by "*". The positions of introns in the corresponding genomic sequence is shown by "m". The composite DNA sequence has been placed in GenBank.

FIG. 5. Genomic Structure of the IT10C3 Gene. Panel A displays a schematic of the exon/intron structure of the IT10C3 locus. Exons I–X are shown as filled boxes. Panel B shows the sequences of the exon-intron junctions, and the sizes of the introns.

FIG. 6. Comparison of IT10C3 with the tetracycline resistance protein of pBR322. The IT10C3 protein sequence was compared with the TGR2_ECOLI sequence using the BESTFIT program of the GCG package (Devereux, J. et al., Nucleic Acids Res. 12:387–395 (1984)). The figure displays the alignment over the first half of each protein, containing the first 6 transmembrane domains. The approximate positions of the transmembrane domains, predicted from the Kyte-Doolittle calculation of hydrophilicity implemented in the PEPTIDESTRUCTURE program, is shown (TM1-6).

DEFINITIONS

Figure 1:
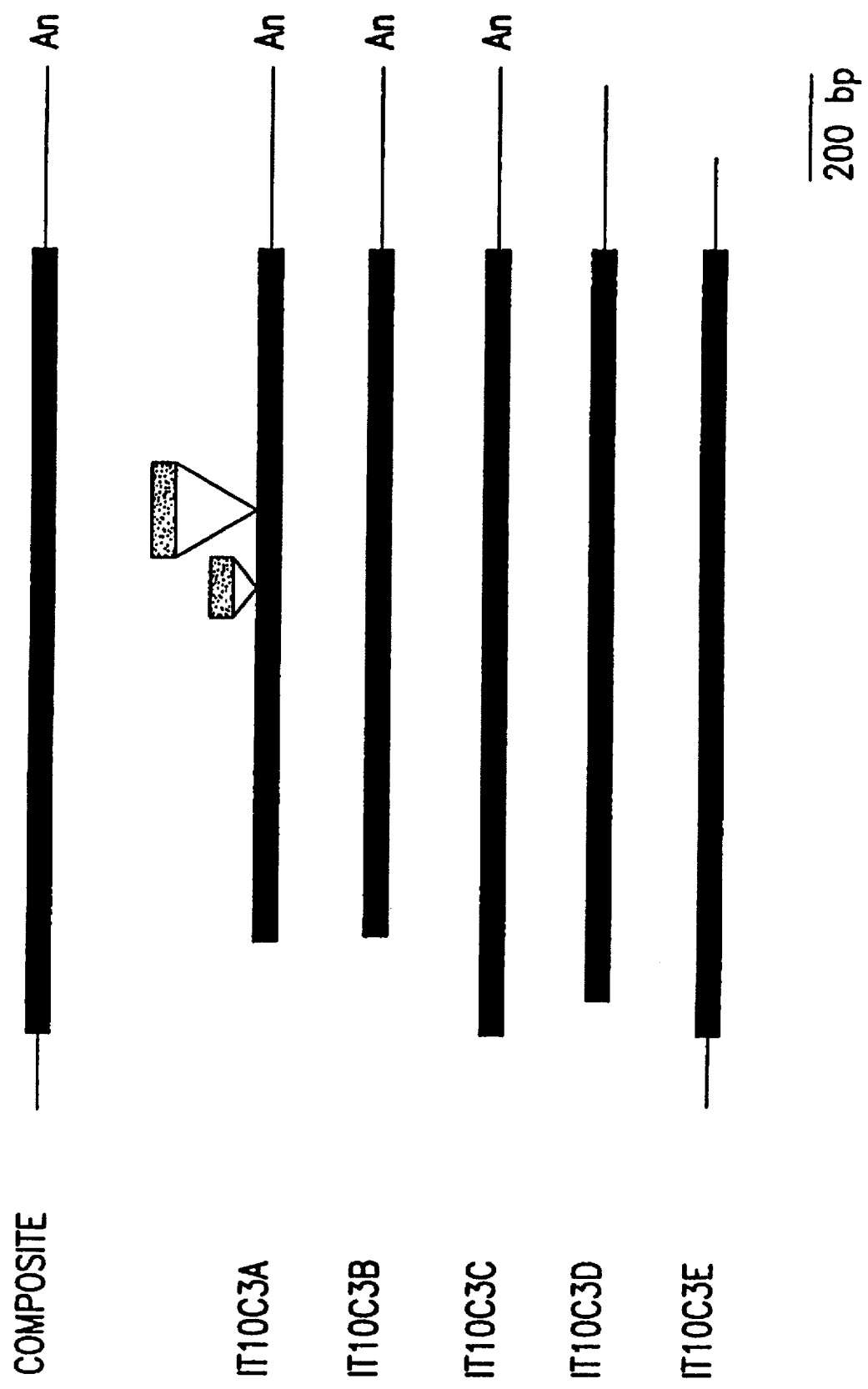
FIG. 1. Schematic of overlapping IT10C3 cDNAs. IT10C3 cDNA clones are shown with their extent of overlap under a composite schematic. The thick bar represents the predicted coding sequence and the poly(A) tail is shown as An. Putative unspliced introns present in IT10C3A are shown as hatched boxes.

In the description that follows, a number of terms used in recombinant DNA (rDNA) technology are extensively utilized. In order to provide a clear and consistent understanding of the specification and claims, including the scope to be given such terms, the following definitions are provided.

Isolated Nucleic Acid Molecule. An "isolated nucleic acid molecule", as is generally understood and used herein, refers to a polymer of nucleotides, and includes but should not be limited to DNA and RNA.

DNA Segment. A DNA segment, as is generally understood and used herein, refers to a molecule comprising a linear stretch of nucleotides wherein the nucleotides are present in a sequence that may encode, through the genetic code, a molecule comprising a linear sequence of amino acid residues that is referred to as a protein, a protein fragment or a polypeptide.

Gene. A DNA sequence related to a single polypeptide chain or protein, and as used herein includes the 5' and 3' untranslated ends. The polypeptide can be encoded by a full-length sequence or any portion of the coding sequence, so long as the functional activity of the protein is retained.

Complementary DNA (cDNA). Recombinant nucleic acid molecules synthesized by reverse transcription of messenger RNA ("mRNA").

Structural Gene. A DNA sequence that is transcribed into mRNA that is then translated into a sequence of amino acids characteristic of a specific polypeptide.

Restriction Endonuclease. A restriction endonuclease (also restriction enzyme) is an enzyme that has the capacity to recognize a specific base sequence (usually 4, 5, or 6 base pairs in length) in a DNA molecule, and to cleave the DNA molecule at every place where this sequence appears. For example, EcoRI recognizes the base sequence GAATTC/CTTAAG.

Restriction Fragment. The DNA molecules produced by digestion with a restriction endonuclease are referred to as restriction fragments. Any given genome may be digested by a particular restriction endonuclease into a discrete set of restriction fragments.

Agarose Gel Electrophoresis. To detect a polymorphism in the length of restriction fragments, an analytical method for fractionating double-stranded DNA molecules on the basis of size is required. The most commonly used technique (though not the only one) for achieving such a fractionation is agarose gel electrophoresis. The principle of this method is that DNA molecules migrate through the gel as though it were a sieve that retards the movement of the largest molecules to the greatest extent and the movement of the smallest molecules to the least extent. Note that the smaller the DNA fragment, the greater the mobility under electrophoresis in the agarose gel.

The DNA fragments fractionated by agarose gel electrophoresis can be visualized directly by a staining procedure if the number of fragments included in the pattern is small. The DNA fragments of genomes can be visualized successfully. However, most genomes, including the human genome, contain far too many DNA sequences to produce a simple pattern of restriction fragments. For example, the human genome is digested into approximately 1,000,000 different DNA fragments by EcoRI. In order to visualize a small subset of these fragments, a methodology referred to as the Southern hybridization procedure Can be applied.

Southern Transfer Procedure. The purpose of the Southern transfer procedure (also referred to as blotting) is to physically transfer DNA fractionated by agarose gel electrophoresis onto a nitrocellulose filter paper or another appropriate surface or method, while retaining the relative positions of DNA fragments resulting from the fractionation procedure. The methodology used to accomplish the transfer from agarose gel to nitrocellulose involves drawing the DNA from the gel into the nitrocellulose paper by capillary action.

Nucleic Acid Hybridization. Nucleic acid hybridization depends on the principle that two single-stranded nucleic acid molecules that have complementary base sequences will reform the thermodynamically favored double-stranded structure if they are mixed under the proper conditions. The double-stranded structure will be formed between two complementary single-stranded nucleic acids even if one is immobilized on a nitrocellulose filter. In the Southern hybridization procedure, the latter situation occurs. As noted previously, the DNA of the individual to be tested is digested with a restriction endonuclease, fractionated by agarose gel electrophoresis, converted to the single-stranded form, and transferred to nitrocellulose paper, making it available for reannealing to the hybridization probe.

Hybridization Probe. To visualize a particular DNA sequence in the Southern hybridization procedure, a labeled DNA molecule or hybridization probe is reacted to the fractionated DNA bound to the nitrocellulose filter. The areas on the filter that carry DNA sequences complementary to the labeled DNA probe become labeled themselves as a consequence of the reannealing reaction. The areas of the filter that exhibit such labeling are visualized. The hybridization probe is generally produced by molecular cloning of a specific DNA sequence.

Oligonucleotide or Oligomer. A molecule comprised of two or more deoxyribonucleofides or ribonucleotides, preferably more than three. Its exact size will depend on many factors, which in turn depend on the ultimate function or use of the oligonucleotide. An oligonucleotide may be derived synthetically or by cloning.

Sequence Amplification. A method for generating large amounts of a target sequence. In general, one or more amplification primers are annealed to a nucleic acid sequence. Using appropriate enzymes, sequences found adjacent to, or in between the primers are amplified.

Amplification Primer. An oligonucleotide which is capable of annealing adjacent to a target sequence and serving as an initiation point for DNA synthesis when placed under conditions in which synthesis of a primer extension product which is complementary to a nucleic acid strand is initiated.

Vector. A plasmid or phage DNA or other DNA sequence into which DNA may be inserted to be cloned. The vector may replicate autonomously in a host cell, and may be further characterized by one or a small number of endonuclease recognition sites at which such DNA sequences may be cut in a determinable fashion and into which DNA may be inserted. The vector may further contain a marker suitable for use in the identification of cells transformed with the vector. Markers, for example, are tetracycline resistance or ampicillin resistance. The words "cloning vehicle" are sometimes used for "vector."

Expression. Expression is the process by which a structural gene produces a polypeptide. It involves transcription of the gene into mRNA, and the translation of such mRNA into polypeptide(s).

Expression Vector. A vector or vehicle similar to a cloning vector but which is capable of expressing a gene which has been cloned into it, after transformation into a host. The cloned gene is usually placed under the control of (i.e., operably linked to) certain control sequences such as promoter sequences.

Expression control sequences will vary depending on whether the vector is designed to express the operably linked gene in a prokaryotic or eukaryotic host and may additionally contain transcriptional elements such as enhancer elements, termination sequences, tissue-specificity elements, and/or translational initiation and termination sites.

Functional Derivative. A "functional derivative" of a sequence, either protein or nucleic acid, is a molecule that possesses a biological activity (either functional or structural) that is substantially similar to a biological activity of the protein or nucleic acid sequence. A functional derivative of a protein may or may not contain post-translational modifications such as covalently linked carbohydrate, depending on the necessity of such modifications for the performance of a specific function. The term "functional derivative" is intended to include the "fragments," "segments," "variants," "analogs," or "chemical derivatives" of a molecule.

As used herein, a molecule is said to be a "chemical derivative" of another molecule when it contains additional chemical moieties not normally a part of the molecule. Such moieties may improve the molecule's solubility, absorption, biological half life, and the like. The moieties may alternatively decrease the toxicity of the molecule, eliminate or attenuate any undesirable side effect of the molecule, and the like. Moieties capable of mediating such effects are disclosed in *Remington's Pharmaceutical Sciences* (1980). Procedures for coupling such moieties to a molecule are well known in the art.

Fragment. A "fragment" of a molecule such as a protein or nucleic acid is meant to refer to any portion of the amino acid or nucleotide genetic sequence.

Variant. A "variant" of a protein or nucleic acid is meant to refer to a molecule substantially similar in structure and biological activity to either the protein or nucleic acid, or to a fragment thereof. Thus, provided that two molecules possess a common activity and may substitute for each other, they are considered variants as that term is used herein even if the composition or secondary, tertiary, or quaternary structure of one of the molecules is not identical to that found in the other, or if the amino acid or nucleotide sequence is not identical.

Analog. An "analog" of a protein or genetic sequence is meant to refer to a protein or genetic sequence substantially similar in function to a protein or genetic sequence described herein.

Allele. An "allele" is an alternative form of a gene occupying a given locus on the chromosome.

Mutation. A "mutation" is any detectable change in the genetic material which may be transmitted to daughter cells and possibly even to succeeding generations giving rise to mutant cells or mutant individuals. If the descendants of a mutant cell give rise only to somatic cells in multicellular organisms, a mutant spot or area of cells arises. Mutations in the germ line of sexually reproducing organisms may be transmitted by the gametes to the next generation resulting in an individual with the new mutant condition in both its somatic and germ cells. A mutation may be any (or a combination of) detectable, unnatural change affecting the chemical or physical constitution, mutability, replication, phenotypic function, or recombination of one or more deoxyribonucleotides; nucleotides may be added, deleted, substituted for, inverted, or transposed to new positions with and without inversion. Mutations may occur spontaneously and can be induced experimentally by application of mutagens. A mutant variation of a nucleic acid molecule results from a mutation. A mutant polypeptide may result from a mutant nucleic acid molecule.

Species. A "species" is a group of actually or potentially interbreeding natural populations. A species variation within a nucleic acid molecule or protein is a change in the nucleic acid or amino acid sequence that occurs among species and may be determined by DNA sequencing of the molecule in question.

Substantially Pure. A "substantially pure" protein or nucleic acid is a protein or nucleic acid preparation that is generally lacking in other cellular components.

DETAILED DESCRIPTION OF THE INVENTION

For purposes of clarity of disclosure, and not by way of limitation, the detailed description of the invention is divided into the following subsections:

I. Isolated Nucleic Acid Molecules Coding for IT10C3 Polypeptides, and Fragments Thereof.

II. Substantially Pure IT10C3 Polypeptides.

III. A Nucleic Acid Probe for the Detection of IT10C3.

IV. A Method of Detecting The Presence of IT10C3 in a Sample.

V. A Kit for Detecting the Presence of IT10C3 in a Sample.

VI. DNA Constructs Comprising a IT10C3 Nucleic Acid Molecule and Cells Containing These Constructs.

VII. An Antibody Having Binding Affinity to an IT10C3 Polypeptide, or a Binding Fragment Thereof and a Hybridoma Containing the Antibody.

VIII. A Method of Detecting an IT10C3 Polypeptide in a Sample.

IX. A Diagnostic Kit Comprising Antibodies to IT10C3.

X. Diagnostic Screening and Treatment

I. Isolated Nucleic Acid Molecules Coding for IT10C3 Polypeptides, and Fragments Thereof.

In one embodiment, the present invention relates to an isolated nucleic acid molecule coding for a polypeptide having an amino acid sequence corresponding to IT10C3, or at least 7 contiguous amino acids thereof (preferably, at least 10, 15, 20, or 30 contiguous amino acids thereof). In one preferred embodiment, the isolated nucleic acid molecule comprises the sequences set forth in SEQ ID NO:1; allelic, mutant or species variation thereof, or at least 18 contiguous nucleotides thereof (preferably at least 20, 25, 30, 35, 40, or 50 contiguous nucleotides thereof). In another preferred embodiment, the isolated nucleic acid molecule encodes the amino acid sequence set forth in SEQ ID NO:2, or mutant or species variation thereof, or at least 7 contiguous amino acids thereof (preferably, at least 10, 15, 20, or 30 contiguous amino acids thereof).

Also included within the scope of this invention are the functional equivalents of the herein-described isolated nucleic acid molecules and derivatives thereof. For example, the nucleic acid sequences depicted in FIG. 3 (SEQ ID NO:1) can be altered by substitutions, additions or deletions that provide for functionally equivalent molecules. Due to the degeneracy of nucleotide coding sequences, other DNA sequences which encode substantially the same amino acid sequence as depicted in FIG. 3 (SEQ ID NO:2) may be used in the practice of the present invention. These include but are not limited to nucleotide sequences comprising all or portions of IT10C3 nucleic acid depicted in FIG. 3 (SEQ ID NO:1) which are altered by the substitution of different codons that encode a functionally equivalent amino acid residue within the sequence, thus producing a silent change.

Such functional alterations of a given nucleic acid sequence afford an opportunity to promote secretion and/or processing of heterologous proteins encoded by foreign nucleic acid sequences fused thereto. All variations of the nucleotide sequence of the IT10C3 genes and fragments thereof permitted by the genetic code are, therefore, included in this invention.

In addition, the nucleic acid sequence may comprise a nucleotide sequence which results from the addition, deletion or substitution of at least one nucleotide to the 5'-end and/or the 3'-end of the nucleic acid formula shown in SEQ ID NO:1 or a derivative thereof. Any nucleotide or polynucleotide may be used in this regard, provided that its addition, deletion or substitution does not alter the amino acid sequence of SEQ ID NO:2 which is encoded by the nucleotide sequence. For example, the present invention is intended to include any nucleic acid sequence resulting from the addition of ATG as an initiation codon at the 5'-end of the inventive nucleic acid sequence or its derivative, or from the addition of TTA, TAG or TGA as a termination codon at the 3'-end of the inventive nucleotide sequence or its derivative. Moreover, the nucleic acid molecule of the present invention may, as necessary, have restriction endonuclease recognition sites added to its 5'-end and/or 3'-end.

Further, it is possible to delete codons or to substitute one or more codons by codons other than degenerate codons to produce a structurally modified polypeptide, but one which has substantially the same utility or activity of the polypeptide produced by the unmodified nucleic acid molecule. As recognized in the art, the two polypeptides are functionally equivalent, as are the two nucleic acid molecules which give rise to their production, even though the differences between the nucleic acid molecules are not related to degeneracy of the genetic code.

A. Isolation of Nucleic Acid.

In one aspect of the present invention, isolated nucleic acid molecules coding for polypeptides having amino acid sequences corresponding to IT10C3 are provided. In particular, the nucleic acid molecule may be isolated from a biological sample containing RNA or DNA.

The nucleic acid molecule may be isolated from a biological sample containing RNA using the techniques of cDNA cloning and subtractive hybridization. The nucleic acid molecule may also be isolated from a cDNA library using a homologous probe.

The nucleic acid molecule may be isolated from a biological sample containing genomic DNA or from a genomic library using techniques well known in the art. Suitable biological samples include, but are not limited to, blood, semen and tissue. The method of obtaining the biological sample will vary depending upon the nature of the sample.

One skilled in the art will realize that the human genome may be subject to slight allelic variations between individuals. Therefore, the isolated nucleic acid molecule is also intended to include allelic variations, so long as the sequence is a functional derivative of the IT10C3 gene. When a human allele does not encode the identical sequence to that of FIG.

3, it can be isolated and identified as IT10C3 using the same techniques used herein, and especially PCR techniques to amplify the appropriate gene with primers based on the sequences disclosed herein. Many polymorphic probes useful in the fine localization of genes on chromosome 4 are known and available (see, for example, "ATCC/NIH Repository Catalogue of Human and Mouse DNA Probes and Libraries," fifth edition, 1991, pages 4–6). Human chromosome 4-specific libraries are known in the art and available from the ATCC for the isolation of probes ("ATCC/NIH Repository Catalogue of Human and Mouse DNA Probes and Libraries," fifth edition, 1991, pages 72–73), for example, LL04NS01 and LL04NS02 (ATCC 57719 and ATCC 57718) are useful for these purposes.

One skilled in the art will realize that organisms other than humans will also contain IT10C3 genes (for example, eukaryotes; more specifically, mammals, birds, fish, and plants; more specifically, gorillas, rhesus monkeys, and chimpanzees). The invention is intended to include, but not be limited to, IT10C3 nucleic acid molecules isolated from the above-described organisms.

B. Synthesis of Nucleic Acid.

Isolated nucleic acid molecules of the present invention are also meant to include those chemically synthesized. For example, a nucleic acid molecule with the nucleotide sequence which codes for the expression product of an IT10C3 gene may be designed and, if necessary, divided into appropriate smaller fragments. Then an oligomer which corresponds to the nucleic acid molecule, or to each of the divided fragments, may be synthesized. Such synthetic oligonucleotides may be prepared, for example, by the triester method of Matteucci et al., *J. Am. Chem. Soc.* 103:3185–3191 (1981) or by using an automated DNA synthesizer.

An oligonucleotide may be derived synthetically or by cloning. If necessary, the 5'-ends of the oligomers may be phosphorylated using T4 polynucleotide kinase. Kinasing of single strands prior to annealing or for labeling may be achieved using an excess of the enzyme. If kinasing is for the labeling of probe, the ATP may contain high specific activity radioisotopes. Then, the DNA oligomer may be subjected to annealing and ligation with T4 ligase or the like.

Substantially Pure IT10C3 Polypeptides.

In another embodiment, the present invention relates to a substantially pure polypeptide having an amino acid sequence corresponding to IT10C3, or a fragment or derivative thereof, or at least 7 contiguous amino acids thereof (preferably, at least 10, 15, 20, or 30 contiguous amino acids thereof), or a functional derivative thereof. In a preferred embodiment, the polypeptide has the amino acid sequence set forth in SEQ ID NO:2, or mutant or species variation thereof, or at least 7 contiguous amino acids thereof (preferably, at least 10, 15, 20, or 30 contiguous amino acids thereof).

Amino acid sequence variants of IT10C3 can be prepared by mutations in the DNA. Such variants include, for example, deletions from, or insertions or substitutions of, residues within the amino acid sequence shown in FIG. 3 (SEQ ID NO:2). Any combination of deletion, insertion, and substitution may also be made to arrive at the final construct, provided that the final construct possesses the desired activity. Obviously, the mutations that will be made in the DNA encoding the variant must not place the sequence out of reading frame and preferably will not create complementary regions that could produce secondary mRNA structure (see EP Patent Application Publication No. 75,444).

While the site for introducing an amino acid sequence variation is predetermined, the mutation per se need not be predetermined. For example, to optimize the performance of a mutation at a given site, random mutagenesis may be conducted at the target codon or region and the expressed IT10C3 variants screened for the optimal combination of desired activity. Techniques for making substitution mutations at predetermined sites in DNA having a known sequence are well known, for example, site-specific mutagenesis.

Preparation of an IT10C3 variant in accordance herewith is preferably achieved by site-specific mutagenesis of DNA that encodes an earlier prepared variant or a nonvariant version of the protein. Site-specific mutagenesis allows the production of IT10C3 variants through the use of specific oligonucleotide sequences that encode the DNA sequence of the desired mutation, as well as a sufficient number of adjacent nucleotides, to provide a primer sequence of sufficient size and sequence complexity to form a stable duplex on both sides of the deletion junction being traversed. Typically, a primer of about 20 to 25 nucleotides in length is preferred, with about 5 to 10 residues on both sides of the junction of the sequence being altered. In general, the technique of site-specific mutagenesis is well known in the art, as exemplified by publications such as Adelman et al., DNA 2:183 (1983).

As will be appreciated, the site-specific mutagenesis technique typically employs a phage vector that exists in both a single-stranded and double-stranded form. Typical vectors useful in site-directed mutagenesis include vectors such as the M13 phage, for example, as disclosed by Messing et al., *Third Cleveland Symposium on Macromolecules and Recombinant DNA*, Editor A. Walton, Elsevier, Amsterdam (1981). These phage are readily commercially available and their use is generally well known to those skilled in the art. Alternatively, plasmid vectors that contain a single-stranded phage origin of replication (Vieira et at., *Meth. Enzymol.* 153:3 (1987)) may be employed to obtain single-stranded DNA.

In general, site-directed mutagenesis in accordance herewith is performed by first obtaining a single-stranded vector that includes within its sequence a DNA sequence that encodes the relevant protein. An oligonucleotide primer bearing the desired mutated sequence is prepared, generally synthetically, for example, by the method of Crea et al., *Proc. Natl. Acad. Sci.* USA 75:5765 (1978). This primer is then annealed with the single-stranded protein-sequence-containing vector, and subjected to DNA-polymerizing enzymes such as *E. coli* polymerase I Klenow fragment, to complete the synthesis of the mutation-bearing strand. Thus, a mutated sequence and the second strand bears the desired mutation. This heteroduplex vector is then used to transform appropriate cells such as JM101 cells and clones are selected that include recombinant vectors beating the mutated sequence arrangement.

After such a clone is selected, the mutated protein region may be removed and placed in an appropriate vector for protein production, generally an expression vector of the type that may be employed for transformation of an appropriate host.

Amino acid sequence deletions generally range from about 1 to 30 residues, more preferably 1 to 10 residues, and typically are contiguous.

Amino acid sequence insertions include amino and/or carboxyl-terminal fusions of from one residue to polypeptides of essentially unrestricted length, as well as intrasequence insertions of single or multiple amino acid residues. Intrasequence insertions (i.e., insertions within the complete hormone receptor molecule sequence) may range generally from about 1 to 10 residues, more preferably 1 to 5. An example of a terminal insertion includes a fusion of a signal sequence, whether heterologous or homologous to the host cell, to the N-terminus of the hormone receptor molecule to facilitate the secretion of mature hormone receptor molecule from recombinant hosts.

The third group of variants are those in which at least one amino acid residue in the hormone receptor molecule, and preferably, only one, has been removed and a different residue inserted in its place. Such substitutions preferably are made in accordance with the following Table 1 when it is desired to modulate finely the characteristics of IT10C3.

TABLE 1

| Original Residue | Exemplary Substitutions |
| --- | --- |
| Ala | gly; ser |
| Arg | lys |
| Asn | gln; his |
| Asp | glu |
| Cys | ser |
| Gln | asn |
| Glu | asp |
| Gly | ala; pro |
| His | asn; gln |
| Ile | leu; val |
| Leu | ile; val |
| Lys | arg; gln; glu |
| Met | leu; tyr; ile |
| Phe | met; leu; tyr |
| Ser | thr |
| Thr | ser |
| Trp | tyr |
| Tyr | trp; phe |
| Val | ile; leu |

Substantial changes in functional or immunological identity are made by selecting substitutions that are less conservative than those in Table 1, i.e., selecting residues that differ more significantly in their effect on maintaining (a) the structure of the polypeptide backbone in the area of the substitution, for example, as a sheet or helical conformation, (b) the charge or hydrophobicity of the molecule at the target site, or (c) the bulk of the side chain. The substitutions that in general are expected to those in which (a) glycine and/or proline is substituted by another amino acid or is deleted or inserted; (b) a hydrophilic residue, e.g., seryl or threonyl, is substituted for (or by) a hydrophobic residue, e.g., leucyl, isoleucyl, phenylalanyl, valyl, or alanyl; (c) a cysteine residue is substituted for (or by) any other residue; (d) a residue having an electropositive side chain, e.g., lysyl, arginyl, or histidyl, is substituted for (or by) a residue having an electronegative charge, e.g., glutamyl or aspartyl; or (e) a residue having a bulky side chain, e.g., phenylalanine, is substituted for (or by) one not having such a side chain, e.g., glycine.

Some deletions, insertions, and substitutions are not expected to produce radical changes in the characteristics of IT10C3. However, when it is difficult to predict the exact effect of the substitution, deletion, or insertion in advance of doing so, one skilled in the art will appreciate that the effect will be evaluated by routine screening assays. For example, a variant typically is made by site-specific mutagenesis of the native IT10C3 encoding-nucleic acid, expression of the variant nucleic acid in recombinant cell culture, and, optionally, purification from the cell culture, for example, by immunoaffinity adsorption on a column (to absorb the variant by binding it to at least one remaining immune epitope). The activity of the cell lysate or purified IT10C3 molecule variant is then screened in a suitable screening assay for the desired characteristic. For example, a change in the immunological character of the IT10C3 molecule, such as affinity for a given antibody, is measured by a competitive type immunoassay. Changes in immunomodulation activity are measured by the appropriate assay. Modifications of such protein properties as redox or thermal stability, hydrophobicity, susceptibility to proteolytic degradation or the tendency to aggregate with carriers or into multimers are assayed by methods well known to the ordinarily skilled artisan.

A variety of methodologies known in the art can be utilized to obtain the peptide of the present invention. In one embodiment, the peptide is purified from tissues or cells which naturally produce the peptide. Alternatively, the above-described isolated nucleic acid fragments could be used to expressed the IT10C3 protein in any organism. The samples of the present invention include cells, protein extracts or membrane extracts of cells, or biological fluids. The sample will vary based on the assay format, the detection method and the nature of the tissues, cells or extracts used as the sample.

Any eukaryotic organism can be used as a source for the peptide of the invention, as long as the source organism naturally contains such a peptide. As used herein, "source organism" refers to the original organism from which the amino acid sequence of the subunit is derived, regardless of the organism the subunit is expressed in and ultimately isolated from.

One skilled in the art can readily follow known methods for isolating proteins in order to obtain the peptide free of natural contaminants. These include, but are not limited to: immunochromoto-graphy, size-exclusion chromatography, HPLC, ion-exchange chromato-graphy, and immuno-affinity chromatography.

III. A Nucleic Acid Probe for the Detection of IT10C3.

In another embodiment, the present invention relates to a nucleic acid probe for the detection of the presence of IT10C3 in a sample comprising the above-described nucleic acid molecules or at least 18 contiguous nucleotides thereof (preferably at least 20, 25, 30, 35, 40, or 50 thereof). In another preferred embodiment, the nucleic acid probe has the nucleic acid sequence set forth in SEQ ID NO:1 or at least 18 contiguous nucleotides thereof (preferably at least 20, 25, 30, 35, 40, or 50 thereof). In another preferred embodiment, the nucleic acid probe encodes the amino acid sequence set forth in SEQ ID NO:2 or at least 7 contiguous amino acids thereof.

In another embodiment, the present invention provides for nucleic acid probes comprising a nucleic acid molecule which is capable of hybridizing to IT10C3 nucleic acid (preferably, the nucleic acid has a sequence substantially as depicted in FIG. 3 (SEQ ID NO:1 ) or portions thereof of at least 18 nucleotides).

The nucleic acid probe may be used to probe an appropriate chromosomal or cDNA library by usual hybridization methods to obtain another nucleic acid molecule of the present invention. A chromosomal DNA or cDNA library may be prepared from appropriate cells according to recognized methods in the art (cf. Molecular Cloning: *A Laboratory Manual*, second edition, edited by Sambrook, Fritsch, & Maniatis, Cold Spring Harbor Laboratory, 1989).

In the alternative, chemical synthesis is carried out in order to obtain nucleic acid probes having nucleotide sequences which correspond to N-terminal and C-terminal portions of the amino acid sequence of the polypeptide of interest. Thus, the synthesized nucleic acid probes may be used as primers in a polymerase chain reaction (PCR) carried out in accordance with recognized PCR techniques, essentially according to PCR Protocols, *A Guide to Methods and Applications*, edited by Michael et al., Academic Press, 1990, utilizing the appropriate chromosomal or cDNA library to obtain the fragment of the present invention.

One skilled in the art can readily design such probes based on the sequence disclosed herein using methods of computer alignment and sequence analysis known in the art (cf. Molecular Cloning: *A Laboratory Manual*, second edition, edited by Sambrook, Fritsch, & Maniatis, Cold Spring Harbor Laboratory, 1989).

The hybridization probes of the present invention can be labeled by standard labeling techniques such as with a radiolabel, enzyme label, fluorescent label, biotin-avidin label, chemiluminescence, and the like. After hybridization, the probes may be visualized using known methods.

The nucleic acid probes of the present invention include RNA, as well as DNA probes, such probes being generated using techniques known in the art.

In one embodiment of the above described method, a nucleic acid probe is immobilized on a solid support. Examples of such solid supports include, but are not limited to, plastics such as polycarbonate, complex carbohydrates such as agarose and sepharose, and acrylic resins, such as polyacrylamide and latex beads. Techniques for coupling nucleic acid probes to such solid supports are well known in the art.

The test samples suitable for nucleic acid probing methods of the present invention include, for example, cells or nucleic acid extracts of cells, or biological fluids. The sample used in the above-described methods will vary based on the assay format, the detection method and the nature of the tissues, cells or extracts to be assayed. Methods for preparing nucleic acid extracts of cells are well known in the art and can be readily adapted in order to obtain a sample which is compatible with the method utilized.

IV. A Method of Detecting The Presence of IT10C3 in a Sample.

In another embodiment, the present invention relates to a method of detecting the presence of IT10C3 in a sample comprising a) contacting said sample with the above-described nucleic acid probe, under conditions such that hybridization occurs, and b) detecting the presence of said probe bound to said nucleic acid molecule. One skilled in the art would select the nucleic acid probe according to techniques known in the art as described above. Samples to be tested include but should not be limited to RNA samples of human tissue.

IT10C3 has been found to be expressed in brain cells. Accordingly, IT10C3 probes may be used detect the presence of RNA from brain cells in a sample. Further, altered expression levels of IT10C3 RNA in an individual, as compared to normal levels, may indicate the presence of disease. The IT10C3 probes may further be used to assay cellular activity in general and specifically in brain tissue.

V. A Kit for Detecting the Presence of IT10C3 in a Sample.

In another embodiment, the present invention relates to a kit for detecting the presence of IT10C3 in a sample comprising at least one container means having disposed therein the above-described nucleic acid probe. In a preferred embodiment, the kit further comprises other containers comprising one or more of the following: wash reagents and reagents capable of detecting the presence of bound nucleic acid probe. Examples of detection reagents include, but are not limited to radiolabelled probes, enzymatic labeled probes (horse radish peroxidase, alkaline phosphatase), and affinity labeled probes (biotin, avidin, or steptavidin).

In detail, a compartmentalized kit includes any kit in which reagents are contained in separate containers. Such containers include small glass containers, plastic containers or strips of plastic or paper. Such containers allow the efficient transfer of reagents from one compartment to another compartment such that the samples and reagents are not cross-contaminated and the agents or solutions of each container can be added in a quantitative fashion from one compartment to another. Such containers will include a container which will accept the test sample, a container which contains the probe or primers used in the assay, containers which contain wash reagents (such as phosphate buffered saline, Tris-buffers, and the like), and containers which contain the reagents used to detect the hybridized probe, bound antibody, amplified product, or the like.

One skilled in the art will readily recognize that the nucleic acid probes described in the present invention can readily be incorporated into one of the established kit formats which are well known in the art.

VI. DNA Constructs Comprising a IT10C3 Nucleic Acid Molecule and Cells Containing These Constructs.

In another embodiment, the present invention relates to a recombinant DNA molecule comprising, 5' to 3', a promoter effective to initiate transcription in a host cell and the above-described nucleic acid molecules. In another embodiment, the present invention relates to a recombinant DNA molecule comprising a vector and an above-described nucleic acid molecules.

In another embodiment, the present invention relates to a nucleic acid molecule comprising a transcriptional region functional in a cell, a sequence complimentary to an RNA sequence encoding an amino acid sequence corresponding to the above-described polypeptide, and a transcriptional termination region functional in said cell.

Preferably, the above-described molecules are isolated and/or purified DNA molecules.

In another embodiment, the present invention relates to a cell or organism that contains an above-described nucleic acid molecule.

In another embodiment, the peptide is purified from cells which have been altered to express the peptide.

As used herein, a cell is said to be "altered to express a desired peptide" when the cell, through genetic manipulation, is made to produce a protein which it normally does not produce or which the cell normally produces at low levels. One skilled in the art can readily adapt procedures for introducing and expressing either genomic, cDNA, or synthetic sequences into either eukaryotic or prokaryotic cells.

A nucleic acid molecule, such as DNA, is said to be "capable of expressing" a polypeptide if it contains nucleotide sequences which contain transcriptional and translational regulatory information and such sequences are "operably linked" to nucleotide sequences which encode the polypeptide. An operable linkage is a linkage in which the regulatory DNA sequences and the DNA sequence sought to be expressed are connected in such a way as to permit gene sequence expression. The precise nature of the regulatory regions needed for gene sequence expression may vary from organism to organism, but shall in general include a promoter region which, in prokaryotes, contains both the promoter (which directs the initiation of RNA transcription) as well as the DNA sequences which, when transcribed into RNA, will signal synthesis initiation. Such regions will normally include those 5'-non-coding sequences involved with initiation of transcription and translation, such as the TATA box, capping sequence, CAAT sequence, and the like.

If desired, the non-coding region 3' to the sequence encoding an IT10C3 gene may be obtained by the above-described methods. This region may be retained for its transcriptional termination regulatory sequences, such as termination and polyadenylation. Thus, by retaining the 3'-region naturally contiguous to the DNA sequence encoding an IT10C3 gene, the transcriptional termination signals may be provided. Where the transcriptional termination signals are not satisfactorily functional in the expression host cell, then a 3' region functional in the host cell may be substituted.

Two DNA sequences (such as a promoter region sequence and an IT10C3 sequence) are said to be operably linked if the nature of the linkage between the two DNA sequences does not (1) result in the introduction of a frame-shift mutation, (2) interfere with the ability of the promoter region sequence to direct the transcription of an IT10C3 gene sequence, or (3) interfere with the ability of the an IT10C3 gene sequence to be transcribed by the promoter region sequence. Thus, a promoter region would be operably linked to a DNA sequence if the promoter were capable of effecting transcription of that DNA sequence.

The present invention encompasses the expression of the IT10C3 gene (or a functional derivative thereof) in either prokaryotic or eukaryotic cells. Prokaryotic hosts are, generally, the most efficient and convenient for the production of recombinant proteins and, therefore, are preferred for the expression of the IT10C3 gene.

Prokaryotes most frequently are represented by various strains of $E.$ $coli.$ However, other microbial strains may also be used, including other bacterial strains. In prokaryotic systems, plasmid vectors that contain replication sites and control sequences derived from a species compatible with the host may be used. Examples of suitable plasmid vectors may include pBR322, pUC118, pUC119 and the like; suitable phage or bacteriophage vectors may include λgt10, λgt11 and the like; and suitable virus vectors may include pMAM-neo, pKRC and the like. Preferably, the selected vector of the present invention has the capacity to replicate in the selected host cell.

Recognized prokaryotic hosts include bacteria such as $E.$ $coli$, Bacillus, Streptomyces, Pseudomonas, Salmonella, Serratia, and the like. However, under such conditions, the peptide will not be glycosylated. The prokaryotic host must be compatible with the replicon and control sequences in the expression plasmid.

To express IT10C3 (or a functional derivative thereof) in a prokaryotic cell, it is necessary to operably link the IT10C3 sequence to a functional prokaryotic promoter. Such promoters may be either constitutive or, more preferably, regulatable (i.e., inducible or derepressible). Examples of constitutive promoters include the int promoter of bacteriophage λ, the bla promoter of the β-lactamase gene sequence of pBR322, and the CAT promoter of the chloramphenicol acetyl transferase gene sequence of pBR325, and the like. Examples of inducible prokaryotic promoters include the major right and left promoters of bacteriophage λ ($P_L$ and $P_R$), the trp, recA, lacZ, lacI, and gal promoters of $E.$ $coli$, the α-amylase (Ulmanen et al., $J.$ $Bacteriol.$ 162:176–182 (1985)) and the δ-28-specific promoters of $B.$ $subtilis$ (Gilman et al., $Gene$ $sequence$ 32:11–20 (1984)), the promoters of the bacteriophages of Bacillus (Gryczan, In: $The$ $Molecular$ $Biology$ $of$ $the$ $Bacilli$, Academic Press, Inc., NY (1982)), and Streptomyces promoters (Ward et al., $Mol.$ $Gen.$ $Genet.$ 203:468–478 (1986)). Prokaryotic promoters are reviewed by Glick ($J.$ $Ind.$ $Microbiol.$ 1:277–282 (1987)); Cenatiempo ($Biochimie$ 68:505–516 (1986)); and Gottesman ($Ann.$ $Rev.$ $Genet.$ 18:415–442 (1984)).

Proper expression in a prokaryotic cell also requires the presence of a ribosome binding site upstream of the gene sequence-encoding sequence. Such ribosome binding sites are disclosed, for example, by Gold et al. ($Ann.$ $Rev.$ $Microbiol.$ 35:365–404 (1981)).

The selection of control sequences, expression vectors, transformation methods, and the like, are dependent on the type of host cell used to express the gene. As used herein, "cell", "cell line", and "cell culture" may be used interchangeably and all such designations include progeny. Thus, the words "transformants" or "transformed cells" include the primary subject cell and cultures derived therefrom, without regard to the number of transfers. It is also understood that all progeny may not be precisely identical in DNA content, due to deliberate or inadvertent mutations. However, as defined, mutant progeny have the same functionality as that of the originally transformed cell.

Host cells which may be used in the expression systems of the present invention are not strictly limited, provided that they are suitable for use in the expression of the IT10C3 peptide of interest. Suitable hosts may often include eukaryotic cells.

Preferred eukaryotic hosts include, for example, yeast, fungi, insect cells, mammalian cells either in vivo, or in tissue culture. Mammalian cells which may be useful as hosts include HeLa cells, cells of fibroblast origin such as VERO or CHO-K1, or cells of lymphoid origin and their derivatives. Preferred mammalian host cells include SP2/0 and J558L, as well as neuroblastoma cell lines such as IMR 332 that may provide better capacities for correct post-translational processing.

In addition, plant cells are also available as hosts, and control sequences compatible with plant cells are available, such as the cauliflower mosaic virus 35S and 19S, and nopaline synthase promoter and polyadenylation signal sequences.

Another preferred host is an insect cell, for example Drosophila larvae. Using insect cells as hosts, the Drosophila alcohol dehydrogenase promoter can be used. Rubin, $Science$ 240:1453–1459 (1988). Alternatively, baculovirus vectors can be engineered to express large amounts of IT10C3 in insects cells (Jasny, $Science$ 238:1653 (1987); Miller et al., In: $Genetic$ $Engineering$ (1986), Setlow, J. K., et al., eds., Plenum, Vol. 8, pp. 277–297).

Different host cells have characteristic and specific mechanisms for the translational and post-translational processing and modification (e.g., glycosylation, cleavage) of proteins. Appropriate cell lines or host systems can be chosen to ensure the desired modification and processing of the foreign protein expressed. For example, expression in a bacterial system can be used to produce an unglycosylated core protein product. Expression in yeast will produce a glycosylated product. Expression in mammalian cells can be used to ensure "native" glycosylation of the heterologous IT10C3 protein. Furthermore, different vector/host expression systems may effect processing reactions such as proteolytic cleavages to different extents.

Any of a series of yeast gene sequence expression systems can be utilized which incorporate promoter and termination elements from the actively expressed gene sequences coding for glycolytic enzymes are produced in large quantities when yeast are grown in mediums rich in glucose. Known glycolytic gene sequences can also provide very efficient transcriptional control signals.

Yeast provides substantial advantages in that it can also carry out post-translational peptide modifications. A number of recombinant DNA strategies exist which utilize strong promoter sequences and high copy number of plasmids which can be utilized for production of the desired proteins in yeast. Yeast recognizes leader sequences on cloned mammalian gene sequence products and secretes peptides bearing leader sequences (i.e., pre-peptides). For a mammalian host, several possible vector systems are available for the expression of IT10C3.

A wide variety of transcriptional and translational regulatory sequences may be employed, depending upon the nature of the host. The transcriptional and translational regulatory signals may be derived from vital sources, such as adenovirus, bovine papilloma virus, simian virus, or the like, where the regulatory signals are associated with a particular gene sequence which has a high level of expression. Alternatively, promoters from mammalian expression products, such as actin, collagen, myosin, and the like, may be employed. Transcriptional initiation regulatory signals may be selected which allow for repression or activation, so that expression of the gene sequences can be modulated. Of interest are regulatory signals which are temperature-sensitive so that by varying the temperature, expression can be repressed or initiated, or are subject to chemical (such as metabolite) regulation.

As discussed above, expression of IT10C3 in eukaryotic hosts requires the use of eukaryotic regulatory regions. Such regions will, in general, include a promoter region sufficient to direct the initiation of RNA synthesis. Preferred eukaryotic promoters include, for example, the promoter of the mouse metallothionein I gene sequence (Hamer et al., *J. Mol. Appl. Gen.* 1:273–288 (1982)); the TK promoter of Herpes virus (McKnight, *Cell* 31:355–365 (1982)); the SV40 early promoter (Benoist et al., *Nature* (London) 290:304–310 (1981)); the yeast gal4 gene sequence promoter (Johnston et al., *Proc. Natl. Acad. Sci.* (USA) 79:6971–6975 (1982); Silver et al., *Proc. Natl. Acad. Sci.* (USA) 81:5951–5955 (1984)).

As is widely known, translation of eukaryotic mRNA is initiated at the codon which encodes the first methionine. For this reason, it is preferable to ensure that the linkage between a eukaryotic promoter and a DNA sequence which encodes IT10C3 (or a functional derivative thereof) does not contain any intervening codons which are capable of encoding a methionine (i.e., AUG). The presence of such codons results either in a formation of a fusion protein (if the AUG codon is in the same reading frame as the IT10C3 coding sequence) or a frame-shift mutation (if the AUG codon is not in the same reading frame as the IT10C3 coding sequence).

An IT10C3 nucleic acid molecule and an operably linked promoter may be introduced into a recipient prokaryotic or eukaryotic cell either as a non-replicating DNA (or RNA) molecule, which may either be a linear molecule or, more preferably, a closed covalent circular molecule. Since such molecules are incapable of autonomous replication, the expression of the gene may occur through the transient expression of the introduced sequence. Alternatively, permanent expression may occur through the integration of the introduced DNA sequence into the host chromosome.

In one embodiment, a vector is employed which is capable of integrating the desired gene sequences into the host cell chromosome. Cells which have stably integrated the introduced DNA into their chromosomes can be selected by also introducing one or more markers which allow for selection of host cells which contain the expression vector. The marker may provide for prototrophy to an auxotrophic host, biocide resistance, e.g., antibiotics, or heavy metals, such as copper, or the like. The selectable marker gene sequence can either be directly linked to the DNA gene sequences to be expressed, or introduced into the same cell by co-transfection. Additional elements may also be needed for optimal synthesis of single chain binding protein mRNA. These elements may include splice signals, as well as transcription promoters, enhancers, and termination signals. cDNA expression vectors incorporating such elements include those described by Okayama, *Molec. Cell. Biol.* 3:280 (1983).

In a preferred embodiment, the introduced nucleic acid molecule will be incorporated into a plasmid or viral vector capable of autonomous replication in the recipient host. Any of a wide variety of vectors may be employed for this purpose. Factors of importance in selecting a particular plasmid or viral vector include: the ease with which recipient cells that contain the vector may be recognized and selected from those recipient cells which do not contain the vector; the number of copies of the vector which are desired in a particular host; and whether it is desirable to be able to "shuttle" the vector between host cells of different species. Preferred prokaryotic vectors include plasmids such as those capable of replication in *E. coli* (such as, for example, pBR322, ColE1, pSC101, pACYC 184, πVX. Such plasmids are, for example, disclosed by Sambrook (cf. *Molecular Cloning: A Laboratory Manual*, second edition, edited by Sambrook, Fritsch, & Maniatis, Cold Spring Harbor Laboratory, 1989)). Bacillus plasmids include pC194, pC221, pT127, and the like. Such plasmids are disclosed by Gryczan (In:. *The Molecular Biology of the Bacilli*, Academic Press, NY (1982), pp. 307–329). Suitable Streptomyces plasmids include pIJ101 (Kendall et al., *J. Bacteriol.* 169:4177–4183 (1987)), and streptomyces bacteriophages such as φC31 (Chater et al., In: *Sixth International Symposium on Actinomycetales Biology*, Akademiai Kaido, Budapest, Hungary (1986), pp. 45–54). Pseudomonas plasmids are reviewed by John et al. (*Rev. Infect. Dis.* 8:693–704 (1986)), and Izaki (*Jpn. J. Bacteriol.* 33:729–742 (1978)).

Preferred eukaryotic plasmids include, for example, BPV, vaccinia, SV40, 2-micron circle, and the like, or their derivatives. Such plasmids are well known in the art (Botstein et al., *Miami Wntr. Symp.* 19:265–274 (1982); Broach, In: *The Molecular Biology of the Yeast Saccharomyces: Life Cycle and Inheritance*, Cold Spring Harbor Laboratory, Cold Spring Harbor, N.Y., p. 445–470 (1981); Broach, *Cell* 28:203–204 (1982); Bollon et al., *J. Clin. Hematol. Oncol.* 10:39–48 (1980); Maniatis, In: *Cell Biology: A Comprehensive Treatise*, Vol. 3, Gene Sequence Expression, Academic Press, NY, pp. 563–608 (1980)).

Once the vector or nucleic acid molecule containing the construct(s) has been prepared for expression, the DNA construct(s) may be introduced into an appropriate host cell by any of a variety of suitable means, i.e., transformation, transfection, conjugation, protoplast fusion, electroporation, particle gun technology, calcium phosphate-precipitation, direct microinjection, and the like. After the introduction of the vector, recipient cells are grown in a selective medium, which selects for the growth of vector-containing cells. Expression of the cloned gene molecule(s) results in the production of IT10C3 or fragments thereof. This can take place in the transformed cells as such, or following the induction of these cells to differentiate (for example, by administration of bromodeoxyuracil to neuroblastoma cells or the like).

VII. An Antibody Having Binding Affinity to an IT10C3 Polypeptide, or a Binding Fragment Thereof and a Hybridoma Containing the Antibody.

In another embodiment, the present invention relates to an antibody having binding affinity to an IT10C3 polypeptide, or a binding fragment thereof. In a preferred embodiment, the polypeptide has the amino acid sequence set forth in SEQ ID NO:2, or mutant or species variation thereof, or at least 7 contiguous amino acids thereof (preferably, at least 10, 15, 20, or 30 contiguous amino acids thereof).

In another preferred embodiment, the present invention relates to an antibody having binding affinity to an IT10C3 polypeptide, or a binding fragment thereof. Those which bind selectively to IT10C3 would be chosen for use in methods which could include, but should not be limited to, the analysis of altered IT10C3 expression in tissue containing IT10C3.

The IT10C3 proteins of the present invention can be used in a variety of procedures and methods, such as for the generation of antibodies, for use in identifying pharmaceutical compositions, and for studying DNA/protein interaction.

The IT10C3 peptide of the present invention can be used to produce antibodies or hybridomas. One skilled in the art will recognize that if an antibody is desired, such a peptide would be generated as described herein and used as an immunogen.

The antibodies of the present invention include monoclonal and polyclonal antibodies, as well fragments of these antibodies. Antibody fragments which contain the idiotype of the molecule can be generated by known techniques. For example, such fragments include but are not limited to: the F(ab')$_2$ fragment; the Fab' fragments, and the Fab fragments.

Of special interest to the present invention are antibodies to IT10C3 (or their functional derivatives) which are produced in humans, or are "humanized" (i.e. non-immunogenic in a human) by recombinant or other technology. Humanized antibodies may be produced, for example by replacing an immunogenic portion of an antibody with a corresponding, but non-immunogenic portion (i.e. chimeric antibodies) (Robinson, R. R. et al., International Patent Publication PCT/US86/02269; Akira, K. et al., European Patent Application 184,187; Taniguchi, M., European Patent Application 171,496; Morrison, S. L. et al., European Patent Application 173,494; Neuberger, M. S. et al., PCT Application WO 86/01533; Cabilly, S. et al., European Patent Application 125,023; Better, M. et al., *Science* 240:1041–1043 (1988); Liu, A. Y. et al., *Proc. Natl. Acad. Sci.* USA 84:3439–3443 (1987); Liu, A. Y. et al., *J. Immunol.* 139:3521–3526 (1987); Sun, L. K. et al., *Proc. Natl. Acad. Sci.* USA 84:214–218 (1987); Nishimura, Y. et al., *Canc. Res.* 47:999–1005 (1987); Wood, C. R. et al., *Nature* 314:446–449 (1985)); Shaw et al., *J. Natl. Cancer Inst.* 80:1553–1559 (1988). General reviews of "humanized" chimeric antibodies are provided by Morrison, S. L. (*Science*, 229:1202–1207 (1985)) and by Oi, V. T. et al., *BioTechniques* 4:214 (1986)). Suitable "humanized" antibodies can be alternatively produced by CDR or CEA substitution (Jones, P. T. et al., *Nature* 321:552–525 (1986); Verhoeyan et al., *Science* 239:1534 (1988); Beidler, C. B. et al., *J. Immunol.* 141:4053–4060 (1988)).

In another embodiment, the present invention relates to a hybridoma which produces the above-described monoclonal antibody, or binding fragment thereof. A hybridoma is an immortalized cell line which is capable of secreting a specific monoclonal antibody.

In general, techniques for preparing monoclonal antibodies and hybridomas are well known in the art (Campbell, "*Monoclonal Antibody Technology: Laboratory Techniques in Biochemistry and Molecular Biology,*" Elsevier Science Publishers, Amsterdam, The Netherlands (1984); St. Groth et al., *J. Immunol. Methods* 35:1–21 (1980)).

Any animal (mouse, rabbit, and the like) which is known to produce antibodies can be immunized with the selected polypeptide. Methods for immunization are well known in the art. Such methods include subcutaneous or interperitoneal injection of the polypeptide. One skilled in the art will recognize that the amount of polypeptide used for immunization will vary based on the animal which is immunized, the antigenicity of the polypeptide and the site of injection.

The polypeptide may be modified or administered in an adjuvant in order to increase the peptide antigenicity. Methods of increasing the antigenicity of a polypeptide are well known in the art. Such procedures include coupling the antigen with a heterologous protein (such as globulin or β-galactosidase) or through the inclusion of an adjuvant during immunization.

For monoclonal antibodies, spleen cells from the immunized animals are removed, fused with myeloma cells, such as SP2/0-Ag14 myeloma cells, and allowed to become monoclonal antibody producing hybridoma cells.

Any one of a number of methods well known in the art can be used to identify the hybridoma cell which produces an antibody with the desired characteristics. These include screening the hybridomas with an ELISA assay, western blot analysis, or radioimmunoassay (Lutz et al., Exp. *Cell Res.* 175:109–124 (1988)).

Hybridomas secreting the desired antibodies are cloned and the class and subclass is determined using procedures known in the art (Campbell, *Monoclonal Antibody Technology: Laboratory Techniques in Biochemistry and Molecular Biology*, supra (1984)).

For polyclonal antibodies, antibody containing antisera is isolated from the immunized animal and is screened for the presence of antibodies with the desired specificity using one of the above-described procedures.

In another embodiment of the present invention, the above-described antibodies are detectably labeled. Antibodies can be detectably labeled through the use of radioisotopes, affinity labels (such as biotin, avidin, and the like), enzymatic labels (such as horse radish peroxidase, alkaline phosphatase, and the like) fluorescent labels (such as FITC or rhodamine, and the like), paramagnetic atoms, and the like. Procedures for accomplishing such labeling are well-known in the art, for example, see (Sternberger et al., *J. Histochem. Cytochem.* 18:315 (1970); Bayer et al., *Meth. Enzym.* 62:308 (1979); Engval et al., *Immunol.* 109:129 (1972); Goding, *J. Immunol. Meth.* 13:215 (1976)). The labeled antibodies of the present invention can be used for in vitro, in vivo, and in situ assays to identify cells or tissues which express a specific peptide.

In another embodiment of the present invention the above-described antibodies are immobilized on a solid support. Examples of such solid supports include plastics such as polycarbonate, complex carbohydrates such as agarose and sepharose, acrylic resins and such as polyacrylamide and latex beads. Techniques for coupling antibodies to such solid supports are well known in the art (Weir et al., "*Handbook of Experimental Immunology*" 4th Ed., Blackwell Scientific Publications, Oxford, England, Chapter 10 (1986); Jacoby et al., Meth. Enzym. 34, Academic Press, New York (1974)). The immobilized antibodies of the present invention can be used for in vitro, in vivo, and in situ assays as well as in immunochromotography.

Furthermore, one skilled in the art can readily adapt currently available procedures, as well as the techniques, methods and kits disclosed above with regard to antibodies, to generate peptides capable of binding to a specific peptide sequence in order to generate rationally designed antipeptide peptides, for example see Hurby et al., "Application of Synthetic Peptides: Antisense Peptides", In *Synthetic Pep-* tides, *A User's Guide*, W. H. Freeman, New York, pp. 289–307 (1992), and Kaspczak et al., *Biochemistry* 28:9230–8 (1989).

Anti-peptide peptides can be generated in one of two fashions. First, the anti-peptide peptides can be generated by replacing the basic amino acid residues found in the IT10C3 peptide sequence with acidic residues, while maintaining hydrophobic and uncharged polar groups. For example, lysine, arginine, and/or histidine residues are replaced with aspartic acid or glutamic acid and glutamic acid residues are replaced by lysine, arginine or histidine.

VIII. A Method of Detecting an IT10C3 Polypeptide in a Sample.

In another embodiment, the present invention relates to a method of detecting an IT10C3 polypeptide in a sample, comprising: a) contacting the sample with an above-described antibody, under conditions such that immunocomplexes form, and b) detecting the presence of said antibody bound to the polypeptide. In detail, the methods comprise incubating a test sample with one or more of the antibodies of the present invention and assaying whether the antibody binds to the test sample. Altered levels of IT10C3 in a sample as compared to normal levels may indicate a specific disease.

Conditions for incubating an antibody with a test sample vary. Incubation conditions depend on the format employed in the assay, the detection methods employed, and the type and nature of the antibody used in the assay. One skilled in the art will recognize that any one of the commonly available immunological assay formats (such as radioimmunoassays, enzyme-linked immunosorbent assays, diffusion based Ouchterlony, or rocket immunofluorescent assays) can readily be adapted to employ the antibodies of the present invention. Examples of such assays can be found in Chard, *"An Introduction to Radioimmunoassay and Related Techniques"* Elsevier Science Publishers, Amsterdam, The Netherlands (1986); Bullock et al., *"Techniques in Immunocytochemistry,"* Academic Press, Orlando, Fla. Vol. 1 (1982), Vol. 2 (1983), Vol. 3 (1985); Tijssen, *"Practice and Theory of Enzyme Immunoassays: Laboratory Techniques in Biochemistry and Molecular Biology,"* Elsevier Science Publishers, Amsterdam, The Netherlands (1985).

The immunological assay test samples of the present invention include cells, protein or membrane extracts of cells, or biological fluids such as blood, serum, plasma, or urine. The test sample used in the above-described method will vary based on the assay format, nature of the detection method and the tissues, cells or extracts used as the sample to be assayed. Methods for preparing protein extracts or membrane extracts of cells are well known in the art and can be readily be adapted in order to obtain a sample which is capable with the system utilized.

IX. A Diagnostic Kit Comprising Antibodies to IT10C3.

In another embodiment of the present invention, a kit is provided which contains all the necessary reagents to carry out the previously described methods of detection. The kit may comprise: i) a first container means containing an above-described antibody, and ii) second container means containing a conjugate comprising a binding partner of the antibody and a label. In another preferred embodiment, the kit further comprises one or more other containers comprising one or more of the following: wash reagents and reagents capable of detecting the presence of bound antibodies. Examples of detection reagents include, but are not limited to, labeled secondary antibodies, or in the alternative, if the primary antibody is labeled, the chromophoric, enzymatic, or antibody binding reagents which are capable of reacting with the labeled antibody. The compartmentalized kit may be as described above for nucleic acid probe kits.

One skilled in the art will readily recognize that the antibodies described in the present invention can readily be incorporated into one of the established kit formats which are well known in the art.

X. Diagnostic Screening and Treatment

It is to be understood that although the following discussion is specifically directed to human patients, the teachings are also applicable to any animal that expresses IT10C3.

The diagnostic and screening methods of the invention are especially useful for a patient suspected of being at risk for developing a disease associated with an altered expression level of IT10C3 based on family history, or a patient in which it is desired to diagnose an IT10C3-related disease.

According to the invention, presymptomatic screening of an individual in need of such screening is now possible using DNA encoding the IT10C3 protein of the invention. The screening method of the invention allows a presymptomatic diagnosis, including prenatal diagnosis, of the presence of a missing or aberrant IT10C3 gene in individuals, and thus an opinion concerning the likelihood that such individual would develop or has developed an IT10C3-associated disease. This is especially valuable for the identification of carriers of altered or missing IT10C3 genes, for example, from individuals with a family history of an IT10C3-associated disease. Early diagnosis is also desired to maximize appropriate timely intervention.

In one preferred embodiment of the method of screening, a tissue sample would be taken from such individual, and screened for (1) the presence of the "normal" human IT10C3 gene; (2) the presence of IT10C3 mRNA and/or (3) the presence of IT10C3 protein. The normal human gene can be characterized based upon, for example, detection of restriction digestion patterns in "normal" versus the patient's DNA, including RFLP analysis, using DNA probes prepared against the IT10C3 sequence (or a functional fragment thereof) taught in the invention. Similarly, IT10C3 mRNA can be characterized and compared to normal IT10C3 mRNA (a) levels and/or (b) size as found in a human population not at risk of developing IT10C3-associated disease using similar probes. Lastly, IT10C3 protein can be (a) detected and/or (b) quantitated using a biological assay for IT10C3 activity or using an immunological assay and IT10C3 antibodies. When assaying IT10C3 protein, the immunological assay is preferred for its speed. An (1) aberrant IT10C3 DNA size pattern, and/or (2) aberrant IT10C3 mRNA sizes or levels and/or (3) aberrant IT10C3 protein levels would indicate that the patient is at risk for developing an IT10C3-associated disease.

The screening and diagnostic methods of the invention do not require that the entire IT10C3 DNA coding sequence be used for the probe. Rather, it is only necessary to use a fragment or length of nucleic acid that is sufficient to detect the presence of the IT10C3 gene in a DNA preparation from a normal or affected individual, the absence of such gene, or an altered physical property of such gene (such as a change in electrophoretic migration pattern).

Prenatal diagnosis can be performed when desired, using any known method to obtain fetal cells, including amniocentesis, chorionic villous sampling (CVS), and fetoscopy. Prenatal chromosome analysis can be used to determine if the portion of the chromosome possessing the normal IT10C3 gene is present in a heterozygous state.

In the method of treating an IT10C3-associated disease in a patient in need of such treatment, functional IT10C3 DNA can be provided to the cells of such patient in a manner and amount that permits the expression of the IT10C3 protein provided by such gene, for a time and in a quantity sufficient to treat such patient. Many vector systems are known in the art to provide such delivery to human patients in need of a gene or protein missing from the cell. For example, retrovirus systems can be used, especially modified retrovirus systems and especially herpes simplex virus systems, such as those described in U.S. Appl. Ser. No. 07/913,977 (filed Jul. 16, 1992); U.S. Appl. Ser. No. 07/956,949 (filed Oct. 6, 1992), U.S. Appl. Ser. No. 07/895,364 (filed Jun. 9, 1992). In addition, such methods are provided for, in, for example, the teachings of Breakefield, X. A. et al., *The New Biologist* 3:203–218 (1991); Huang, Q. et al., *Experimental Neurology* 115:303–316 (1992), WO 93/03743 and WO 90/09441. Delivery of a DNA sequence encoding a functional IT10C3 protein, such as the amino acid encoding sequence of FIG. 3, will effectively replace the missing or mutated IT10C3 gene of the invention.

In another embodiment, the present invention relates to a method of administering IT10C3 to an animal (preferably, a mammal (specifically, a human)) in an amount sufficient to effect an altered level of IT10C3 in said animal. The administered IT10C3 could specifically effect IT10C3 associated functions. Further, since IT10C3 is expressed in brain tissue, administration of IT10C3 could be used to alter IT10C3 levels in the brain.

One skilled in the art will appreciate that the amounts to be administered for any particular treatment protocol can readily be determined. The dosage should not be so large as to cause adverse side effects, such as unwanted cross-reactions, anaphylactic reactions, and the like. Generally, the dosage will vary with the age, condition, sex and extent of disease in the patient, counter indications, if any, and other such variables, to be adjusted by the individual physician. Dosage can vary from 0.001 mg/kg to 50 mg/kg of IT10C3, in one or more administrations daily, for one or several days. IT10C3 can be administered parenterally by injection or by gradual perfusion over time. It can be administered intravenously, intraperitoneally, intramuscularly, or subcutaneously.

Preparations for parenteral administration include sterile or aqueous or non-aqueous solutions, suspensions, and emulsions. Examples of nonaqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose and sodium chloride, lactated Ringer's, or fixed oils. Intravenous vehicles include fluid and nutrient replenishers, electrolyte replenishers, such as those based on Ringer's dextrose, and the like. Preservatives and other additives may also be present, such as, for example, antimicrobials, antioxidants, chelating agents, inert gases and the like. See, generally, *Remington's Pharmaceutical Science*, 16th Ed., Mack Eds. (1980).

In another embodiment, the present invention relates to a pharmaceutical composition comprising IT10C3 in an amount sufficient to alter IT10C3 associated activity, and a pharmaceutically acceptable diluent, carrier, or excipient. Appropriate concentrations and dosage unit sizes can be readily determined by one skilled in the art as described above (See, for example, *Remington's Pharmaceutical Sciences* (16th ed., Osol, A., Ed., Mack, Easton PA (1980) and WO 91/19008).

The present invention is described in further detail in the following non-limiting examples.

EXAMPLES

The following protocols and experimental details are referenced in the examples that follow.

Exon amplification and cDNA cloning. The exon amplification procedure was used to isolate coding sequences from the cosmid Y24 as described (Buckler, A. J. et al., *Proc. Natl. Acad. Sci.* USA 88:4005–4009 (1991); Taylor, S. A. M. et al., *Nature Genet.* 2:223–227 (1992)). Amplified exon products were used to screen a lambda zapII human frontal cortex cDNA library, producing IT10C3A. Additional cDNA clones were obtained by using IT10C3A to reprobe the same library.

DNA sequence analysis. Double stranded sequencing of cDNA clones were performed by alkali denaturation of the template and the use of the dideoxy-chain termination method (Sanger, T. et al., *Proc. Natl. Acad. Sci.* USA 74:5463–5467 (1977)). Direct cosmid sequencing was performed to determine intron/exon boundaries as described (McClatchey, A. I. et al., *Hum. Mol. Genet.* 1:521–527 (1992)). Oligonucleotides for sequencing were synthesized using an automated DNA synthesizer (Applied Biosystems).

Isolation of RNA and Northern analysis. Total RNA was extracted from human lymphoblast cell lines, human brain and from various baboon tissues (brain, spleen, liver, kidney, heart and testis), as described (Maniatis, T. et al., Molecular Cloning: *A Laboratory Manual*, Cold Spring Harbor Laboratory Press (1982)). 10 μg of total RNA from each sample was used to prepare Northern blots by electrophoresis through 1.2% agarose-formaldehyde gels (Maniatis, T. et al., Molecular Cloning: *A Laboratory Manual*, Cold Spring Harbor Laboratory Press (1982)) and transferring to Hybond N membrane (Amersham). Hybridizations were carried out in 50% formamide, 5×SSC, 2× Denhardt's solution and 0.1% SDS at 42° C. The filters were washed to 0.2×SSC and 0.1% SDS at 65° C. before exposing to X-Omat XAR film (Kodak).

EXAMPLE 1

Cloning of IT10C3

The application of exon amplification to cosmid Y24 which maps distal to D4S95 within the HD candidate region has been previously reported (Taylor, S. A. M. et al., *Nature Genet.* 2:223–227 (1992)). In the initial study, screening of a human frontal cortex cDNA library with a mixture of uncloned trapped exon PCR products identified α-adducin cDNA clones. An additional cDNA clone, IT10C3A, unrelated to α-adducin, has been isolated using exons from the same cosmid. For further characterization of this novel gene, the library was reprobed with IT10C3A, yielding four independent cDNA clones, IT10C3B-E (FIG. 1).

Figure 2:
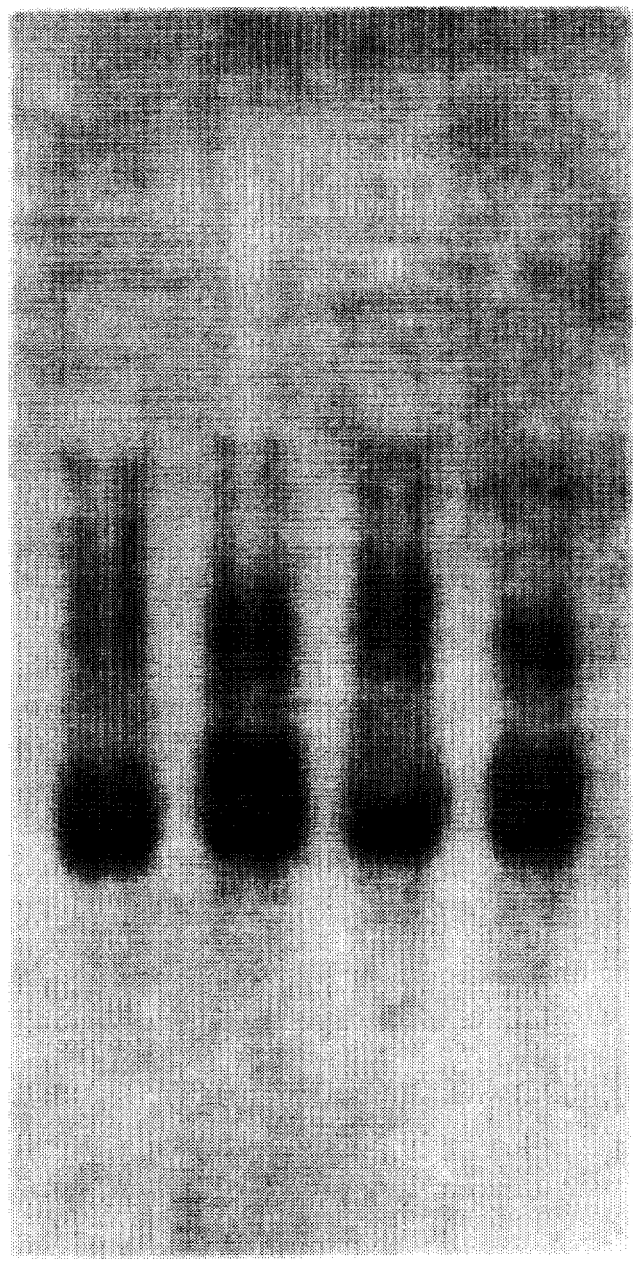
FIG. 2. Northern blot hybridization of IT10C3. IT10C3A was hybridized to total RNA from four independent human lymphoblast cell lines (lanes 1–4), in order to determine the expected size of a full-length cDNA clone. The probe detected an RNA of approximately 1.8 kb. The positions of 28S and 18S ribosomal RNAs are indicated.

Northern blot analysis using IT10C3A revealed an approximately 2 kb transcript in total RNA from human lymphoblasts (FIG. 2). A similar-sized RNA was also detected in human brain and in various baboon tissues (spleen, liver, heart, kidney, and testis). The composite sequence of the IT10C3 transcript was determined by analysis of the five cDNA clones shown schematically in FIG. 1. The final sequence spans 1,788 base pairs, including a poly(A)-tail of 29 residues (FIG. 3). A Met codon at base 121, occurring within a context of a Kozak consensus sequence (Kozak, M., *Nucleic Acids Res.* 12:857–872 (1984)), begins an open reading frame of 1365 bases predicting a 48 kD protein. An in-frame stop codon occurs within 50 bp upstream from putative initiator ATG. The original IT10C3A clone appears to represent an incompletely spliced version of the transcript since it contains two apparent introns of 108 bases and 160 bases after residues 923 and 1034 of FIG. 3 (see below).

EXAMPLE 2

Genomic Organization of the IT10C3 Gene

Figure 4:
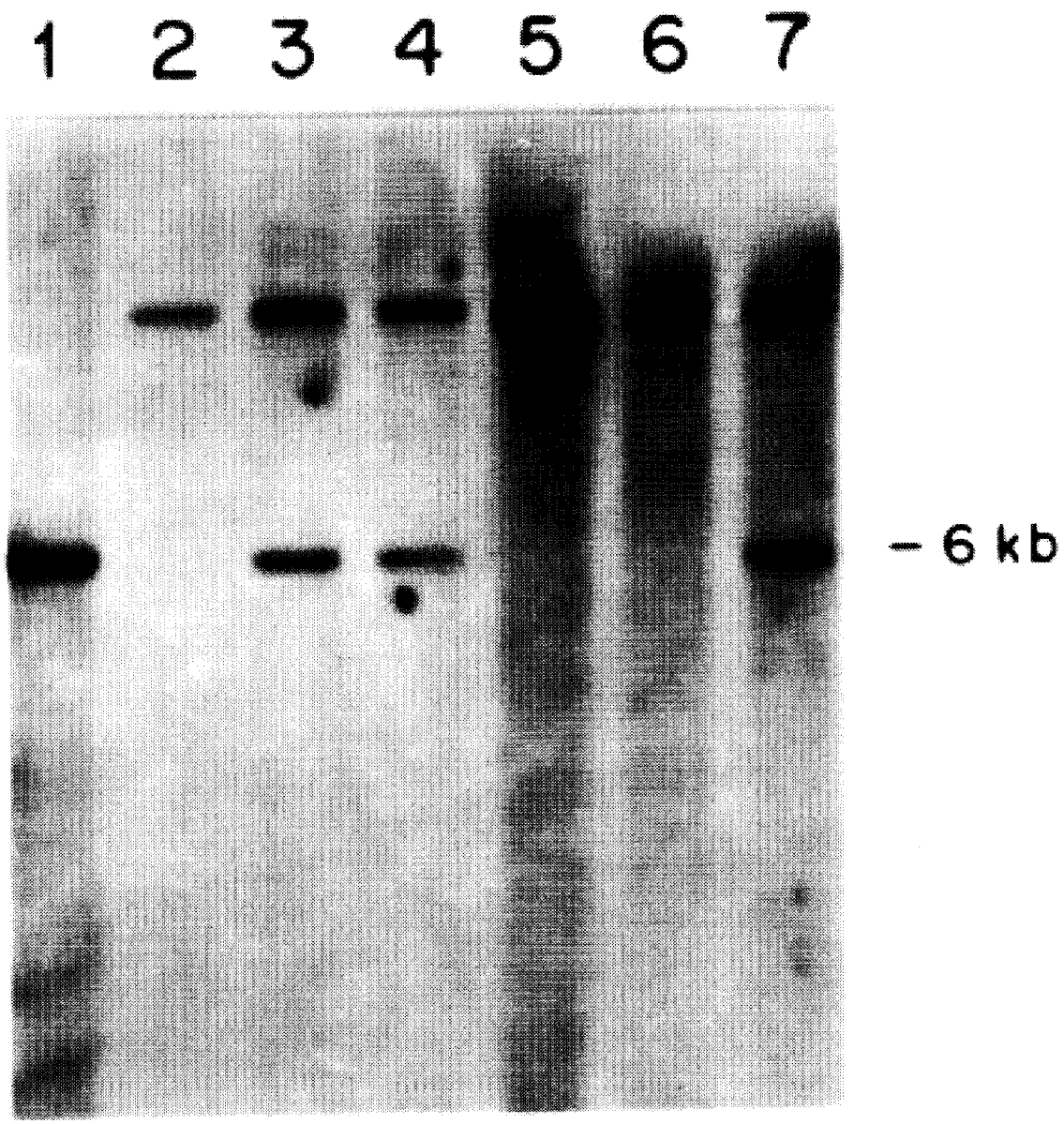
FIG. 4. Mapping of IT10C3 within 4p16.3. Somatic cell hybrid lines which comprise a regional mapping panel of 4p16.3 have been described previously (Lin, C. S. et al., Somat. Cell Mol. Genet. 17:481–488 (1991); MacDonald, M. E. et al., Genomics 1:29–34 (1987); Smith, B. et al., Am. J. Hum. Genet. 42:335–344 (1988)). IT10C3A was hybridized to a genomic blot of HindIII-digested DNA from the following: Lane 1, human lymphoblast; lane 2, hamster DNA; lane 3, hybrid HHW416 containing an intact chromosome 4 as its only human material; lane 4, HHW661 containing 4pter-4p15.1; lane 5, HHW842 containing approximately the most telomeric 2 Mb 4p16.3 but missing the proximal portion due to an interstitial deletion; lane 6, HHW847 containing a t(4;21) translocation that deletes all of 4p16.3; and lane 7, HHW1071 containing a t(4;12) translocation that retains about 3 Mb at the telomere of 4P. IT10C3 A is confined to a single 6 kb HindIII fragment that maps to the 1.2 Mb region in the central portion of 4p16.3 that is present in HHW1071, but absent from HHW842, and from HHW847.

IT10C3 is confined to a 6 kb HindIII fragment mapping to the expected central portion of 4p16.3 based on a regional somatic cell hybrid panel (FIG. 4). Direct sequencing of the overlapping cosmids Y24 and 17E10 was used to determine the genomic organization of the IT10C3 gene (McClatchey, A. I. et al., *Hum. Mol. Genet.* 1:521–527 (1992)) which spans approximately 3,200 bp. Based on cDNA clones IT10B-E, there are 10 exons in the IT10C3 gene with the putative initiation codon located in exon 1 and the stop codon located in the last exon (FIG. 5, panel A). Consensus splice sites were found at the intron/exon boundaries (FIG. 5, panel B). The two extra segments present in IT10C3A correspond to the introns separating exons 6 and 7 and exons 7 and 8, respectively. It is conceivable that the apparently unspliced sequence corresponding to IT10C3A could be translated to generate an altered protein. The extra segment corresponding to the 6/7 intron maintains the reading frame and would add 36 amino acids to the protein after codon 267. The second segment (the 7/8 intron) would introduce 14 amino acids after codon 304, but then would truncate the protein with a new stop codon.

EXAMPLE 3

Similarity to a Superfamily of Transporters

A comparison of the IT10C3 cDNA sequence with the GenBank database using both the Genetics Computer Group (GCG) Sequence Analysis Software Package (Devereux, J. et al., *Nucleic Acids Res.* 12:387–395 (1984)), and the BLAST network service of the National Center for Biotechnology Information (Altschul, S. F., *J. Mol. Biol.* 217:403–410 (1990)) did not identify significant similarity to any previously reported DNA sequence. However, the translated sequence of the open reading frame revealed a striking similarity to a superfamily of bacterial antibiotic drug resistance transporters. The strongest similarity is to the tetracycline resistance protein encoded by the cloning vector pBR322 (TCR2_ECOLI) in the SwissProt database P-3.9e$^{-16}$, 34% identity over 103 amino acids).

In *E. coli*, tetracycline resistance is usually conferred by a plasmid-borne gene encoding an antiporter that actively pumps the antibiotic (in combination with a divalent cation) out of the cell in exchange for H$^+$ (Levy, S. B., *Am. Soc. Microbiol.* News 54:418–421 (1988); Yamaguchi, A. et al., *FEBS Lett.* 282:415–418 (1991)). There are several different tetracycline efflux proteins which display 47–79% sequence identity with each other. Extensive investigation of the tetracycline efflux proteins has revealed a characteristic structure, composed of N-terminal and C-terminal halves, each possessing 6 transmembrane domains. This "6+6" structure has been proposed as a common feature of the "Major Facilitator Superfamily", currently composed of more than 50 related proteins comprising both active and passive small molecule transporters from many species of bacteria, plants and animals (Marger, N. D. and Saier, M. H. Jr., TIBS 18:13–20 (1993)).

The predicted protein encoded by the IT10C3 cDNAs displays similarity to all of the tetracycline efflux proteins of *E. coli* (TCR1_ECOLI, TCR2_ECOLI, TCR3_ECOLI in SwissProt and RA1TETD, L06798 in GenBank) and has an overall sequence consistent with the "6+6" structure of 12 transmembrane domains. The similarity with the tet proteins is largely confined to a first half of the molecule, corresponding to the first six transmembrane segments (FIG. 6). This region also exhibits similarity with several other members of the superfamily, including the fluoroquinolone resistance norA protein of *Staphylococcus aereus* (NORA_STAAU), and the multidrug resistance protein of *Bacillus subtilis* (A39705 in the PIR database). Weak similarity was also detected with a family of mammalian insulin-responsive glucose transporters (GTR4_HUMAN, GTR4_MOUSE, GTR4_RAT).

Interestingly, another family of mammalian transporters that displays sequence similarity with the tet proteins has recently been reported (Liu, Y. et at., *Cell* 70:539–551 (1992)). The rat chromaffin granule amine transporter and the rat synaptic vesicle amine transporter are both related to the tet proteins over the first six transmembrane domains, although more distantly than IT10C3. The amine transporters also possess a hydrophilic loop between transmembrane domains 1 and 2 that is not present in the tet genes nor in mammalian plasma membrane amine transporters. A direct comparison of the IT10C3 protein with the chromaffin granule and synaptic vesicle amine transporters revealed a patch of sequence similarity (40–44% identity over 27 residues) corresponding to transmembrane domain 1, but no extended sequence similarity over the rest of the proteins. The IT10C3 protein does display a hydrophilic loop in the same position as those amine transporters, but it is not related by sequence.

The IT10C3 sequence apparently encodes a novel mammalian member of the tetracycline resistance protein superfamily, and acts as a transporter for a small molecule. This putative transporter is expressed in brain and might therefore play a role in neural function or nerve cell viability.

All publications mentioned hereinabove are hereby incorporated in their entirety by reference.

While the foregoing invention has been described in some detail for purposes of clarity and understanding, it will be appreciated by one skilled in the art from a reading of this disclosure that various changes in form and detail can be made without departing from the true scope of the invention and appended claims.

What is claimed is:

1. An isolated nucleic acid molecule coding for a polypeptide comprising an amino acid sequence encoded by IT10C3.

2. The isolated nucleic acid molecule according to claim 1, wherein the nucleic acid molecule has the nucleic acid sequence set forth in SEQ ID NO:1 which encodes the amino acid sequence set forth in SEQ ID NO:2.

3. The isolated nucleic acid molecule according to claim 1, wherein the molecule encodes the amino acid sequence set forth in SEQ ID NO:2.

4. A nucleic acid probe for specifically detecting the presence of IT10C3 in a DNA sample from an individual comprising a nucleic acid molecule sufficient to specifically detect the presence of IT10C3 in said sample, wherein the molecule has the nucleic acid sequence set forth in SEQ ID NO:1, or at least 18 contiguous nucleotides thereof.

5. A nucleic acid probe for specifically detecting the presence of IT10C3 in a DNA sample from an individual comprising a nucleic acid molecule sufficient to specifically detect the presence of IT10C3 in said sample, wherein the probe encodes the amino acid sequence set forth in SEQ ID NO:2, or at least 7 contiguous amino acids thereof.

6. A method of detecting IT10C3 nucleic acid in a sample comprising:
   a) contacting said sample with the nucleic acid probe according to claim 4 or 5, under conditions such that hybridization occurs specifically to IT10C3 nucleic acid in said sample, and
   b) detecting the presence of said probe bound to IT10C3 nucleic acid.

7. A kit for detecting the presence of IT10C3 nucleic acid in a sample comprising at least one container means having disposed therein the nucleic acid probe according to claim 4 or 5.

8. A recombinant nucleic acid molecule comprising, 5' to 3', a promoter effective to initiate transcription in a host cell and the isolated nucleic acid molecule according to claim 1.

9. A recombinant nucleic acid molecule comprising a vector and the isolated nucleic acid molecule according to claim 1.

10. A host cell that contains the recombinant nucleic acid molecule according to claims 8 or 9.

* * * * *

SEQUENCE LISTING ( 1 ) GENERAL INFORMATION:

( i i i ) NUMBER OF SEQUENCES: 21

( 2 ) INFORMATION FOR SEQ ID NO:1:

( i ) SEQUENCE CHARACTERISTICS:
        ( A ) LENGTH: 1788 base pairs
        ( B ) TYPE: nucleic acid
        ( C ) STRANDEDNESS: both
        ( D ) TOPOLOGY: linear ( i x ) FEATURE:
        ( A ) NAME/KEY: CDS
        ( B ) LOCATION: 121..1488

( x i ) SEQUENCE DESCRIPTION: SEQ ID NO:1:

```
CGCCCCTTTA GGGTGCTCGC CGGCTGTCGG GTGTGGGGGT ATGCCAGGCC CCGGAGGACT    60

CGGCTTCCCC GCTAACCCGA CCCGCCGCAC CCCACCCAGG CCAGGTCAGA GCAGCCCACC   120

ATG GGA TGG GGA GGG GGT GGA GGC TGC ACC CCC CGC CCA CCC ATC CAC    168
Met Gly Trp Gly Gly Gly Gly Gly Cys Thr Pro Arg Pro Pro Ile His
 1               5                  10                  15

CAG CAG CCG CCG GAG CGC CGC GTG GTC ATC GTT GTC TTT CTC GGC CTC    216
Gln Gln Pro Pro Glu Arg Arg Val Val Ile Val Val Phe Leu Gly Leu
             20                  25                  30

CTG CTG GAC CTC CTG GCC TTC ACG CTG CTG CTG CCC CTG CTG CCC GGG    264
Leu Leu Asp Leu Leu Ala Phe Thr Leu Leu Leu Pro Leu Leu Pro Gly
         35                  40                  45

CTG TTG GAG AGC CAC GGC CGT GCC CAC GAC CCC CTC TAT GGC TCC TGG    312
Leu Leu Glu Ser His Gly Arg Ala His Asp Pro Leu Tyr Gly Ser Trp
     50                  55                  60

CAG GGC GGG GTG GAC TGG TTT GCC ACC GCC ATC GGG ATG CCA GTG GAG    360
Gln Gly Gly Val Asp Trp Phe Ala Thr Ala Ile Gly Met Pro Val Glu
 65                  70                  75                  80

AAG AGG TAC AAC AGT GTC CTG TTC GGA GGT CTC ATT GGC TCG GCA TTC    408
Lys Arg Tyr Asn Ser Val Leu Phe Gly Gly Leu Ile Gly Ser Ala Phe
                 85                  90                  95

TCT GTC CTG CAG TTT CTG TGT GCG CCA CTC ACT GGG GCC ACC TCT GAC    456
Ser Val Leu Gln Phe Leu Cys Ala Pro Leu Thr Gly Ala Thr Ser Asp
            100                 105                 110

TGC TTG GGG AGG CGC CCG GTG ATG CTG CTG TGC CTG ATG GGT GTG GCC    504
Cys Leu Gly Arg Arg Pro Val Met Leu Leu Cys Leu Met Gly Val Ala
        115                 120                 125

ACC TCA TAT GCA GTC TGG GCC ACC TCT CGG AGC TTT GCG GCC TTC CTG    552
Thr Ser Tyr Ala Val Trp Ala Thr Ser Arg Ser Phe Ala Ala Phe Leu
    130                 135                 140

GCC TCC AGG CTG ATT GGG GGC ATC AGC AAA GGG AAC GTC AGC CTC TCC    600
Ala Ser Arg Leu Ile Gly Gly Ile Ser Lys Gly Asn Val Ser Leu Ser
145                 150                 155                 160

ACG GCC ATC GTT GCT GAC CTG GGC TCG CCT CTG GCC CGC AGT CAA GGC    648
Thr Ala Ile Val Ala Asp Leu Gly Ser Pro Leu Ala Arg Ser Gln Gly
                165                 170                 175

ATG GCG GTC ATT GGG GTG GCC TTC TCA CTG GGC TTC ACC CTG GGC CCT    696
Met Ala Val Ile Gly Val Ala Phe Ser Leu Gly Phe Thr Leu Gly Pro
            180                 185                 190

ATG CTC GGA GCC TCC CTG CCC CTG GAA ATG GCA CCC TGG TTT GCC CTG    744
Met Leu Gly Ala Ser Leu Pro Leu Glu Met Ala Pro Trp Phe Ala Leu
        195                 200                 205

CTC TTC GCA GCC TCC GAC CTG CTG TTC ATC TTC TGC TTC CTG CCA GAG    792
Leu Phe Ala Ala Ser Asp Leu Leu Phe Ile Phe Cys Phe Leu Pro Glu
    210                 215                 220

ACG CTG CCC CTG GAG AAA CGG GCG CCC TCT ATC GCC CTG GGG TTC CGT    840
Thr Leu Pro Leu Glu Lys Arg Ala Pro Ser Ile Ala Leu Gly Phe Arg
225                 230                 235                 240

GAT GCG GCT GAT CTG CTC AGC CCC CTG GCC CTG CTG CGC TTC TCG GCT    888
Asp Ala Ala Asp Leu Leu Ser Pro Leu Ala Leu Leu Arg Phe Ser Ala
```

|     |     |     |     |     |     |     |     |     |     |     |     |     |     |     |     |      |
|---|---|---|---|---|---|---|---|---|---|---|---|---|---|---|---|---|
|     |     |     |     | 245 |     |     |     |     | 250 |     |     |     |     | 255 |     |      |
| GTC | GCT | CGT | GGC | CAG | GAC | CCA | CCC | TCT | GGA | GAC | AGG | CTC | AGC | AGC | CTG | 936  |
| Val | Ala | Arg | Gly<br>260 | Gln | Asp | Pro | Pro | Ser<br>265 | Gly | Asp | Arg | Leu | Ser<br>270 | Ser | Leu |      |
| CGC | CGC | CTG | GGC | CTA | GTC | TAC | TTC | CTC | TAC | CTC | TTC | CTG | TTC | TCG | GGC | 984  |
| Arg | Arg | Leu<br>275 | Gly | Leu | Val | Tyr | Phe | Leu<br>280 | Tyr | Leu | Phe | Leu | Phe<br>285 | Ser | Gly |      |
| CTG | GAG | TAC | ACG | CTG | AGC | TTC | CTC | ACA | CAC | CAG | CGC | TTC | CAG | TTC | AGT | 1032 |
| Leu | Glu<br>290 | Tyr | Thr | Leu | Ser | Phe<br>295 | Leu | Thr | His | Gln | Arg<br>300 | Phe | Gln | Phe | Ser |      |
| AGC | CTA | CAG | CAG | GGG | AAG | ATG | TTT | TTC | CTC | ATC | GGC | CTC | ACC | ATG | GCC | 1080 |
| Ser<br>305 | Leu | Gln | Gln | Gly | Lys<br>310 | Met | Phe | Phe | Leu | Ile<br>315 | Gly | Leu | Thr | Met | Ala<br>320 |      |
| ACC | ATC | CAG | GGT | GCC | TAT | GCC | CGG | CGG | ATC | CAC | CCT | GGC | GGG | GAA | GTT | 1128 |
| Thr | Ile | Gln | Gly | Ala<br>325 | Tyr | Ala | Arg | Arg | Ile<br>330 | His | Pro | Gly | Gly | Glu<br>335 | Val |      |
| GCT | GCC | GTG | AAG | CGG | GCC | CTC | CTG | CTG | GTG | CCC | GCC | TTC | CTC | CTC | | 1176 |
| Ala | Ala | Val | Lys<br>340 | Arg | Ala | Leu | Leu | Leu<br>345 | Val | Pro | Ala | Phe<br>350 | Leu | Leu |  |      |
| ATC | GGC | TGG | GGA | CGT | TCT | CTG | CCC | GTG | CTG | GGC | CTG | GGG | CTG | CTG | CTC | 1224 |
| Ile | Gly | Trp<br>355 | Gly | Arg | Ser | Leu | Pro<br>360 | Val | Leu | Gly | Leu<br>365 | Gly | Leu | Leu | Leu |      |
| TAC | TCC | TTT | GCC | GCC | GCC | GTT | GTG | GTG | CCC | TGC | CTG | TCC | TCC | GTG | GTC | 1272 |
| Tyr | Ser<br>370 | Phe | Ala | Ala | Ala | Val<br>375 | Val | Val | Pro | Cys | Leu<br>380 | Ser | Ser | Val | Val |      |
| GCT | GGC | TAT | GGC | TCA | CCA | GGG | CAG | AAG | GGC | ACG | GTC | ATG | GGT | ACA | CTG | 1320 |
| Ala<br>385 | Gly | Tyr | Gly | Ser | Pro<br>390 | Gly | Gln | Lys | Gly | Thr<br>395 | Val | Met | Gly | Thr | Leu<br>400 |      |
| CGC | AGC | CTA | GGT | GCT | CTG | GCC | AGG | GCC | GCG | GGG | CCC | CTG | GTG | GCC | GCT | 1368 |
| Arg | Ser | Leu | Gly | Ala<br>405 | Leu | Ala | Arg | Ala | Ala<br>410 | Gly | Pro | Leu | Val | Ala<br>415 | Ala |      |
| TCA | GTG | TAC | TGG | CTG | GCC | GGG | GCC | CAG | GCC | TGC | TTC | ACC | ACG | TGG | TCC | 1416 |
| Ser | Val | Tyr | Trp<br>420 | Leu | Ala | Gly | Ala | Gln<br>425 | Ala | Cys | Phe | Thr | Thr<br>430 | Trp | Ser |      |
| GGG | CTC | TTT | TTG | CTC | CCC | TTC | TTC | CTC | CTG | CAG | AAG | CTG | AGT | TAC | CCG | 1464 |
| Gly | Leu | Phe<br>435 | Leu | Leu | Pro | Phe | Phe<br>440 | Leu | Leu | Gln | Lys | Leu<br>445 | Ser | Tyr | Pro |      |
| GCA | CAG | ACG | CTC | AAG | GCT | GAG | TAGCTGAGCC | | ACTGTGCCCA | | GGCTGTGGGC | | | | | 1515 |
| Ala | Gln | Thr<br>450 | Leu | Lys | Ala | Glu<br>455 | | | | | | | | | |      |

ACCAGGCAGA GTGGGAGCCT AGGTCAGGCC CCTGCCCACT GCCTGACCCC CACCCCCCGC 1575

CAGTCCAGGG AGACCCTGTG GGTGGGGGCC GGCCCCTAAG CAGGAAGCTC AGGCAGCTCC 1635

TCCAGACTTA CTTACTCCTT CAGTGACTCC GAGCTGCAGC ACTCCAAGGC TGTCAGGGCT 1695

TCTGTTTGTT TTTTAAACTA TGCACCAGGT TTCTGATGAT GAAATAAAGC ACCTGTTTGT 1755

TTTAAAAAAA AAAAAAAAA AAAAAAAAA AAA 1788

( 2 ) INFORMATION FOR SEQ ID NO:2:

( i ) SEQUENCE CHARACTERISTICS:
        ( A ) LENGTH: 455 amino acids
        ( B ) TYPE: amino acid
        ( D ) TOPOLOGY: linear ( i i ) MOLECULE TYPE: protein ( x i ) SEQUENCE DESCRIPTION: SEQ ID NO:2:

Met Gly Trp Gly Gly Gly Gly Cys Thr Pro Arg Pro Pro Ile His
 1               5                  10                  15

Gln Gln Pro Pro Glu Arg Arg Val Val Ile Val Val Phe Leu Gly Leu

|   |   |   |   |   | 20 |   |   |   | 25 |   |   |   | 30 |   |   |
|---|---|---|---|---|---|---|---|---|---|---|---|---|---|---|---|
| Leu | Leu | Asp 35 | Leu | Leu | Ala | Phe | Thr 40 | Leu | Leu | Leu | Pro 45 | Leu | Leu | Pro | Gly |
| Leu | Leu 50 | Glu | Ser | His | Gly | Arg 55 | Ala | His | Asp | Pro 60 | Leu | Tyr | Gly | Ser | Trp |
| Gln 65 | Gly | Gly | Val | Asp | Trp 70 | Phe | Ala | Thr | Ala 75 | Ile | Gly | Met | Pro | Val | Glu 80 |
| Lys | Arg | Tyr | Asn | Ser 85 | Val | Leu | Phe | Gly | Gly 90 | Leu | Ile | Gly | Ser | Ala 95 | Phe |
| Ser | Val | Leu | Gln 100 | Phe | Leu | Cys | Ala | Pro 105 | Leu | Thr | Gly | Ala | Thr 110 | Ser | Asp |
| Cys | Leu | Gly 115 | Arg | Arg | Pro | Val | Met 120 | Leu | Leu | Cys | Leu | Met 125 | Gly | Val | Ala |
| Thr | Ser 130 | Tyr | Ala | Val | Trp | Ala 135 | Thr | Ser | Arg | Ser | Phe 140 | Ala | Ala | Phe | Leu |
| Ala 145 | Ser | Arg | Leu | Ile | Gly 150 | Gly | Ile | Ser | Lys | Gly 155 | Asn | Val | Ser | Leu | Ser 160 |
| Thr | Ala | Ile | Val | Ala 165 | Asp | Leu | Gly | Ser | Pro 170 | Leu | Ala | Arg | Ser | Gln 175 | Gly |
| Met | Ala | Val | Ile 180 | Gly | Val | Ala | Phe | Ser 185 | Leu | Gly | Phe | Thr | Leu 190 | Gly | Pro |
| Met | Leu | Gly 195 | Ala | Ser | Leu | Pro | Leu 200 | Glu | Met | Ala | Pro | Trp 205 | Phe | Ala | Leu |
| Leu | Phe 210 | Ala | Ala | Ser | Asp | Leu 215 | Leu | Phe | Ile | Phe | Cys 220 | Phe | Leu | Pro | Glu |
| Thr 225 | Leu | Pro | Leu | Glu | Lys 230 | Arg | Ala | Pro | Ser | Ile 235 | Ala | Leu | Gly | Phe | Arg 240 |
| Asp | Ala | Ala | Asp | Leu 245 | Leu | Ser | Pro | Leu | Ala 250 | Leu | Leu | Arg | Phe | Ser 255 | Ala |
| Val | Ala | Arg | Gly 260 | Gln | Asp | Pro | Pro | Ser 265 | Gly | Asp | Arg | Leu | Ser 270 | Ser | Leu |
| Arg | Arg | Leu 275 | Gly | Leu | Val | Tyr | Phe 280 | Leu | Tyr | Leu | Phe | Leu 285 | Phe | Ser | Gly |
| Leu | Glu 290 | Tyr | Thr | Leu | Ser | Phe 295 | Leu | Thr | His | Gln | Arg 300 | Phe | Gln | Phe | Ser |
| Ser 305 | Leu | Gln | Gln | Gly | Lys 310 | Met | Phe | Phe | Leu | Ile 315 | Gly | Leu | Thr | Met | Ala 320 |
| Thr | Ile | Gln | Gly | Ala 325 | Tyr | Ala | Arg | Arg | Ile 330 | His | Pro | Gly | Gly | Glu 335 | Val |
| Ala | Ala | Val | Lys 340 | Arg | Ala | Leu | Leu | Leu 345 | Leu | Val | Pro | Ala | Phe 350 | Leu | Leu |
| Ile | Gly | Trp 355 | Gly | Arg | Ser | Leu | Pro 360 | Val | Leu | Gly | Leu | Gly 365 | Leu | Leu | Leu |
| Tyr | Ser 370 | Phe | Ala | Ala | Ala | Val 375 | Val | Val | Pro | Cys | Leu 380 | Ser | Ser | Val | Val |
| Ala 385 | Gly | Tyr | Gly | Ser | Pro 390 | Gly | Gln | Lys | Gly | Thr 395 | Val | Met | Gly | Thr | Leu 400 |
| Arg | Ser | Leu | Gly | Ala 405 | Leu | Ala | Arg | Ala | Ala 410 | Gly | Pro | Leu | Val | Ala 415 | Ala |
| Ser | Val | Tyr | Trp 420 | Leu | Ala | Gly | Ala | Gln 425 | Ala | Cys | Phe | Thr | Thr 430 | Trp | Ser |
| Gly | Leu | Phe 435 | Leu | Leu | Pro | Phe | Phe 440 | Leu | Leu | Gln | Lys | Leu 445 | Ser | Tyr | Pro |

```
Ala Gln Thr Leu Lys Ala Glu
    450                 455
```

( 2 ) INFORMATION FOR SEQ ID NO:3:

( i ) SEQUENCE CHARACTERISTICS:
        ( A ) LENGTH: 12 base pairs
        ( B ) TYPE: nucleic acid
        ( C ) STRANDEDNESS: both
        ( D ) TOPOLOGY: linear ( x i ) SEQUENCE DESCRIPTION: SEQ ID NO:3:

GCCCACGTGA GT                                                                  12

( 2 ) INFORMATION FOR SEQ ID NO:4:

( i ) SEQUENCE CHARACTERISTICS:
        ( A ) LENGTH: 12 base pairs
        ( B ) TYPE: nucleic acid
        ( C ) STRANDEDNESS: both
        ( D ) TOPOLOGY: linear ( x i ) SEQUENCE DESCRIPTION: SEQ ID NO:4:

CCCTAGGACC CC                                                                  12

( 2 ) INFORMATION FOR SEQ ID NO:5:

( i ) SEQUENCE CHARACTERISTICS:
        ( A ) LENGTH: 12 base pairs
        ( B ) TYPE: nucleic acid
        ( C ) STRANDEDNESS: both
        ( D ) TOPOLOGY: linear ( x i ) SEQUENCE DESCRIPTION: SEQ ID NO:5:

TCGGAGGTAT GG                                                                  12

( 2 ) INFORMATION FOR SEQ ID NO:6:

( i ) SEQUENCE CHARACTERISTICS:
        ( A ) LENGTH: 12 base pairs
        ( B ) TYPE: nucleic acid
        ( C ) STRANDEDNESS: both
        ( D ) TOPOLOGY: linear ( x i ) SEQUENCE DESCRIPTION: SEQ ID NO:6:

TCTCAGGTCT CA                                                                  12

( 2 ) INFORMATION FOR SEQ ID NO:7:

( i ) SEQUENCE CHARACTERISTICS:
        ( A ) LENGTH: 12 base pairs
        ( B ) TYPE: nucleic acid
        ( C ) STRANDEDNESS: both
        ( D ) TOPOLOGY: linear ( x i ) SEQUENCE DESCRIPTION: SEQ ID NO:7:

TGCCTGGTAT GT                                                                  12

( 2 ) INFORMATION FOR SEQ ID NO:8:

( i ) SEQUENCE CHARACTERISTICS:
        ( A ) LENGTH: 12 base pairs
        ( B ) TYPE: nucleic acid
        ( C ) STRANDEDNESS: both
        ( D ) TOPOLOGY: linear ( x i ) SEQUENCE DESCRIPTION: SEQ ID NO:8:

GGGCAGATGG GT                                                                  12

( 2 ) INFORMATION FOR SEQ ID NO:9:

( i ) SEQUENCE CHARACTERISTICS:
        ( A ) LENGTH: 12 base pairs
        ( B ) TYPE: nucleic acid
        ( C ) STRANDEDNESS: both
        ( D ) TOPOLOGY: linear ( x i ) SEQUENCE DESCRIPTION: SEQ ID NO:9:

GGCATGGTAA GT                                                                                                   12

( 2 ) INFORMATION FOR SEQ ID NO:10:

( i ) SEQUENCE CHARACTERISTICS:
        ( A ) LENGTH: 12 base pairs
        ( B ) TYPE: nucleic acid
        ( C ) STRANDEDNESS: both
        ( D ) TOPOLOGY: linear ( x i ) SEQUENCE DESCRIPTION: SEQ ID NO:10:

CCCTAGGCGG TC                                                                                                12

( 2 ) INFORMATION FOR SEQ ID NO:11:

( i ) SEQUENCE CHARACTERISTICS:
        ( A ) LENGTH: 12 base pairs
        ( B ) TYPE: nucleic acid
        ( C ) STRANDEDNESS: both
        ( D ) TOPOLOGY: linear ( x i ) SEQUENCE DESCRIPTION: SEQ ID NO:11:

AAACGGGTAG GG                                                                                                12

( 2 ) INFORMATION FOR SEQ ID NO:12:

( i ) SEQUENCE CHARACTERISTICS:
        ( A ) LENGTH: 12 base pairs
        ( B ) TYPE: nucleic acid
        ( C ) STRANDEDNESS: both
        ( D ) TOPOLOGY: linear ( x i ) SEQUENCE DESCRIPTION: SEQ ID NO:12:

CCACAGGCGG TC                                                                                                12

( 2 ) INFORMATION FOR SEQ ID NO:13:

( i ) SEQUENCE CHARACTERISTICS:
        ( A ) LENGTH: 12 base pairs
        ( B ) TYPE: nucleic acid
        ( C ) STRANDEDNESS: both
        ( D ) TOPOLOGY: linear ( x i ) SEQUENCE DESCRIPTION: SEQ ID NO:13:

AGACAGTAAG GA                                                                                                12

( 2 ) INFORMATION FOR SEQ ID NO:14:

( i ) SEQUENCE CHARACTERISTICS:
        ( A ) LENGTH: 12 base pairs
        ( B ) TYPE: nucleic acid
        ( C ) STRANDEDNESS: both
        ( D ) TOPOLOGY: linear ( x i ) SEQUENCE DESCRIPTION: SEQ ID NO:14:

CCCAGGGCTC AG                                                                                                12

( 2 ) INFORMATION FOR SEQ ID NO:15:

( i ) SEQUENCE CHARACTERISTICS:
        ( A ) LENGTH: 12 base pairs
        ( B ) TYPE: nucleic acid
        ( C ) STRANDEDNESS: both
        ( D ) TOPOLOGY: linear ( x i ) SEQUENCE DESCRIPTION: SEQ ID NO:15:

CAGTAGGTGG GT                                        12

( 2 ) INFORMATION FOR SEQ ID NO:16:

( i ) SEQUENCE CHARACTERISTICS:
        ( A ) LENGTH: 12 base pairs
        ( B ) TYPE: nucleic acid
        ( C ) STRANDEDNESS: both
        ( D ) TOPOLOGY: linear ( x i ) SEQUENCE DESCRIPTION: SEQ ID NO:16:

TCCCAGCCTA CA                                        12

( 2 ) INFORMATION FOR SEQ ID NO:17:

( i ) SEQUENCE CHARACTERISTICS:
        ( A ) LENGTH: 12 base pairs
        ( B ) TYPE: nucleic acid
        ( C ) STRANDEDNESS: both
        ( D ) TOPOLOGY: linear ( x i ) SEQUENCE DESCRIPTION: SEQ ID NO:17:

AAGCGGGTAG GG                                        12

( 2 ) INFORMATION FOR SEQ ID NO:18:

( i ) SEQUENCE CHARACTERISTICS:
        ( A ) LENGTH: 12 base pairs
        ( B ) TYPE: nucleic acid
        ( C ) STRANDEDNESS: both
        ( D ) TOPOLOGY: linear ( x i ) SEQUENCE DESCRIPTION: SEQ ID NO:18:

CTGCAGGCCC TC                                        12

( 2 ) INFORMATION FOR SEQ ID NO:19:

( i ) SEQUENCE CHARACTERISTICS:
        ( A ) LENGTH: 12 base pairs
        ( B ) TYPE: nucleic acid
        ( C ) STRANDEDNESS: both
        ( D ) TOPOLOGY: linear ( x i ) SEQUENCE DESCRIPTION: SEQ ID NO:19:

CTTCAGGTAG GG                                        12

( 2 ) INFORMATION FOR SEQ ID NO:20:

( i ) SEQUENCE CHARACTERISTICS:
        ( A ) LENGTH: 12 base pairs
        ( B ) TYPE: nucleic acid
        ( C ) STRANDEDNESS: both
        ( D ) TOPOLOGY: linear ( x i ) SEQUENCE DESCRIPTION: SEQ ID NO:20:

CCGCAGTGTA CT                                        12

( 2 ) INFORMATION FOR SEQ ID NO:21:

( i ) SEQUENCE CHARACTERISTICS:
   ( A ) LENGTH: 222 amino acids
   ( B ) TYPE: amino acid
   ( D ) TOPOLOGY: linear ( x i ) SEQUENCE DESCRIPTION: SEQ ID NO:21:

| Ser | Asn | Asn | Ala | Leu | Ile | Val | Ile | Leu | Gly | Thr | Val | Thr | Leu | Asp | Ala |
| 1 | | | | 5 | | | | | 10 | | | | | 15 | |
| Val | Gly | Ile | Gly | Leu | Val | Met | Pro | Val | Leu | Pro | Gly | Leu | Leu | Arg | Asp |
| | | | 20 | | | | | 25 | | | | | 30 | | |
| Ile | Val | His | Ser | Asp | Ser | Ile | Ala | Ser | His | Tyr | Gly | Val | Leu | Leu | Ala |
| | | 35 | | | | | 40 | | | | | 45 | | | |
| Leu | Tyr | Ala | Leu | Met | Gln | Phe | Leu | Cys | Ala | Pro | Val | Leu | Gly | Ala | Leu |
| | 50 | | | | | 55 | | | | | 60 | | | | |
| Ser | Asp | Arg | Phe | Gly | Arg | Arg | Pro | Val | Leu | Leu | Ala | Ser | Leu | Leu | Gly |
| 65 | | | | 70 | | | | | 75 | | | | | | 80 |
| Ala | Thr | Ile | Asp | Tyr | Ala | Ile | Met | Ala | Thr | Thr | Pro | Val | Leu | Trp | Ile |
| | | | | 85 | | | | | 90 | | | | | 95 | |
| Leu | Tyr | Ala | Gly | Arg | Ile | Val | Ala | Gly | Ile | Thr | Gly | Ala | Thr | Gly | Ala |
| | | | 100 | | | | | 105 | | | | | 110 | | |
| Val | Ala | Gly | Ala | Tyr | Ile | Ala | Asp | Ile | Thr | Asp | Gly | Glu | Asp | Arg | Ala |
| | | 115 | | | | | 120 | | | | | 125 | | | |
| Arg | His | Phe | Gly | Leu | Met | Ser | Ala | Cys | Phe | Gly | Val | Gly | Met | Val | Ala |
| | 130 | | | | | 135 | | | | | 140 | | | | |
| Gly | Pro | Val | Ala | Gly | Gly | Leu | Leu | Gly | Ala | Ile | Ser | Leu | His | Ala | Pro |
| 145 | | | | | 150 | | | | | 155 | | | | | 160 |
| Phe | Leu | Ala | Ala | Ala | Val | Leu | Asn | Gly | Leu | Asn | Leu | Leu | Leu | Gly | Cys |
| | | | | 165 | | | | | 170 | | | | | 175 | |
| Phe | Leu | Met | Gln | Glu | Ser | His | Lys | Gly | Glu | Arg | Arg | Pro | Met | Pro | Leu |
| | | | 180 | | | | | 185 | | | | | 190 | | |
| Arg | Ala | Phe | Asn | Pro | Val | Ser | Ser | Phe | Arg | Trp | Ala | Arg | Gly | Met | Thr |
| | | 195 | | | | | 200 | | | | | 205 | | | |
| Ile | Val | Ala | Ala | Leu | Met | Thr | Val | Phe | Phe | Ile | Met | Gln | Leu | | |
| | 210 | | | | | 215 | | | | | 220 | | | | |